(12) United States Patent
Yamada

(10) Patent No.: US 11,992,231 B2
(45) Date of Patent: May 28, 2024

(54) SYSTEM AND METHOD FOR SOFT TISSUE AND BONE REPAIR

(71) Applicant: Ronald Yamada, Orangevale, CA (US)

(72) Inventor: Ronald Yamada, Orangevale, CA (US)

(*) Notice: Subject to any disclaimer, the term of this patent is extended or adjusted under 35 U.S.C. 154(b) by 419 days.

(21) Appl. No.: 17/492,149

(22) Filed: Oct. 1, 2021

(65) Prior Publication Data
US 2023/0103416 A1 Apr. 6, 2023

(51) Int. Cl.
| | | |
|---|---|---|
| *A61B 17/17* | (2006.01) | |
| *A61B 17/00* | (2006.01) | |
| *A61B 17/16* | (2006.01) | |
| *A61B 17/34* | (2006.01) | |
| *A61F 2/30* | (2006.01) | |
| *A61F 2/46* | (2006.01) | |

(52) U.S. Cl.
CPC .... *A61B 17/1778* (2016.11); *A61B 17/00234* (2013.01); *A61B 17/1684* (2013.01); *A61B 17/3468* (2013.01); *A61F 2/30756* (2013.01); *A61F 2/4618* (2013.01); *A61B 2017/00323* (2013.01); *A61F 2002/4635* (2013.01)

(58) Field of Classification Search
CPC .......... A61B 17/1778; A61B 17/00234; A61B 17/1684; A61B 17/3468; A61B 17/1764; A61B 17/3421; A61B 17/3462; A61B 17/3417; A61B 2017/00323; A61B 2017/3447; A61B 2017/3454; A61F 2/30756; A61F 2/4618; A61F 2002/4635
USPC .................... 606/79–80; 604/164.01, 164.11
See application file for complete search history.

(56) References Cited

U.S. PATENT DOCUMENTS

| | | | | |
|---|---|---|---|---|
| 10,251,639 | B1* | 4/2019 | Yamada | A61B 17/0469 |
| 2004/0073227 | A1* | 4/2004 | Dreyfuss | A61B 17/1778 |
| | | | | 606/96 |
| 2005/0137600 | A1* | 6/2005 | Jacobs | A61B 17/1631 |
| | | | | 606/79 |
| 2006/0074434 | A1* | 4/2006 | Wenstrom, Jr. | A61B 17/17 |
| | | | | 606/96 |
| 2008/0275453 | A1* | 11/2008 | Lafosse | A61B 17/1796 |
| | | | | 623/13.14 |
| 2008/0306487 | A1* | 12/2008 | Hart | A61B 17/1714 |
| | | | | 606/96 |
| 2009/0281545 | A1* | 11/2009 | Stubbs | A61F 2/32 |
| | | | | 623/22.21 |
| 2011/0208194 | A1* | 8/2011 | Steiner | A61B 17/1675 |
| | | | | 606/80 |

(Continued)

*Primary Examiner* — Jessica Weiss
(74) *Attorney, Agent, or Firm* — Duane Morris LLP

(57) ABSTRACT

A soft tissue and bone repair system and corresponding method are provided which are particularly useful for labral repairs in the human shoulder. The system comprises at least two guide cannulae capable of being introduced into an anatomical structure of a human body at different entry points for repair of a tear in soft tissue. A pulling line can be passed within the anatomical structure between the guide cannulae. A guide device may be attached to the pulling line and inserted into one of the guide cannula. The guide device is capable of delivering a drilling device into the anatomical structure. The pulling line is capable of being pulled to move an end of the guide device from a one location to another within the anatomical structure to position the drilling device on a desired drilling path to access the tear in soft tissue.

10 Claims, 20 Drawing Sheets

(56) References Cited

U.S. PATENT DOCUMENTS

2012/0239086 A1* 9/2012 Reznik ............... A61B 17/0401
606/232
2018/0125531 A1* 5/2018 Yamada ................ A61B 17/12
2022/0287728 A1* 9/2022 Cournoyer ......... A61B 17/1739

* cited by examiner

SYSTEM AND METHOD FOR SOFT TISSUE AND BONE REPAIR

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

The present disclosure relates generally to medical devices, and more specifically to a system and method for soft tissue and bone repair.

SUMMARY

In accordance with embodiments of the present disclosure, novel and useful soft tissue and bone repair systems and methods are provided, which can be particularly useful for labral repairs in the human shoulder. According to some embodiments, the systems and methods use a kedging line to pull and hold a guide device to repair labrum tears that are difficult to reach without suboptimal drilling into the glenoid bone or risking injury in the neurovascular zone, as required with previously developed pushed devices used in conventional surgical techniques. In some embodiments, the systems and methods of the present disclosure can employ a highly angulated guide cannula to improve accessing a tear (e.g., of the labrum) and inserting an implant at a site of the tear while held stationary at the glenoid bone, thus minimizing a destabilizing shear force as compared to conventional devices that require pushing.

BRIEF DESCRIPTION OF THE DRAWINGS

FIGS. 7a-1 illustrate a method of use of a system for soft tissue and bone repair, according to some embodiments.

Figure 1:
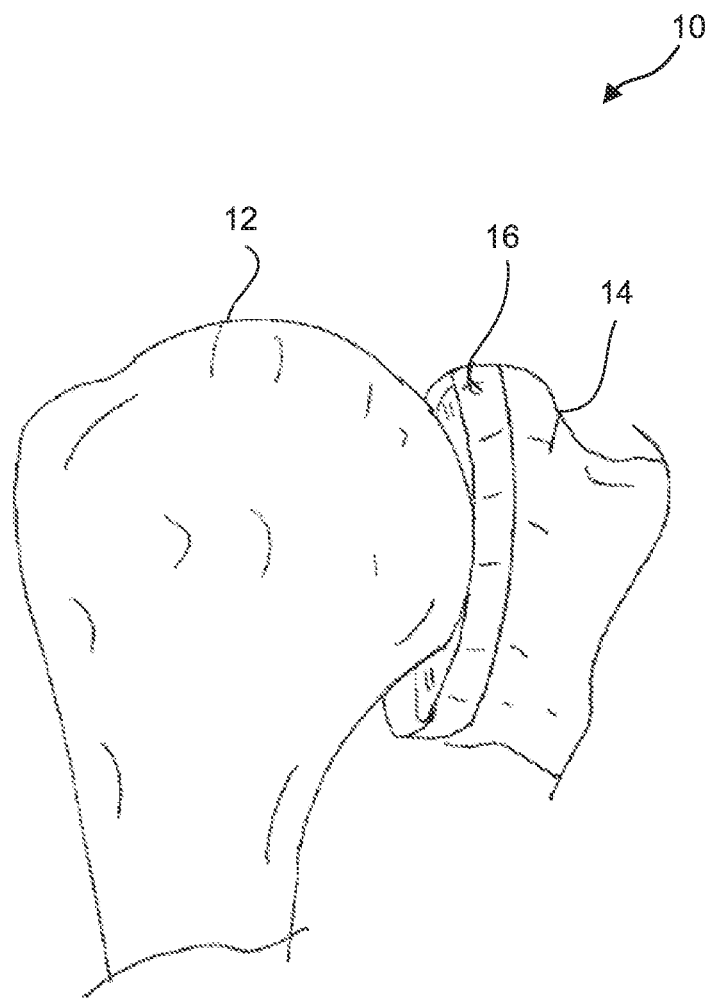
FIG. 1 illustrates a portion of the anatomy of the human shoulder.

In the figures, elements having the same designations have the same or similar functions.

DETAILED DESCRIPTION

This description and the accompanying drawings that illustrate aspects, embodiments, implementations, or applications should not be taken as limiting—the claims define the protected invention. Various mechanical, compositional, structural, and operational changes may be made without departing from the spirit and scope of this description and the claims. In some instances, well-known components, structures, or techniques have not been shown or described in detail as these are known to one skilled in the art. Like numbers in two or more figures represent the same or similar elements. It should be understood that the items illustrated in the drawing figures are not necessarily to scale.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

The subject matter discussed in this application or section should not be assumed to be prior art. The subject matter in this section merely represents different approaches, which in and of themselves may also be inventions.

Shoulder Joint

Embodiments of the present disclosure may operate or be applied to make repairs to soft tissue and bone, for example, such as present in a human shoulder joint.

Referring to FIG. 1, the shoulder joint 10 in the human anatomy includes an upper arm bone (humerus) 12 that rests in a shallow socket of the shoulder blade (glenoid bone) 14. Each shoulder joint 10 of the human anatomy also includes a joint capsule composed of connective tissue that stabilizes the shoulder while allowing a great range of motion during the use of the human arm. The head of the humerus 12 is typically larger than the glenoid 14 and a soft tissue rim, referred to as the labrum 16, surrounds the glenoid 14 to help stabilize the shoulder joint 10.

Figure 2:
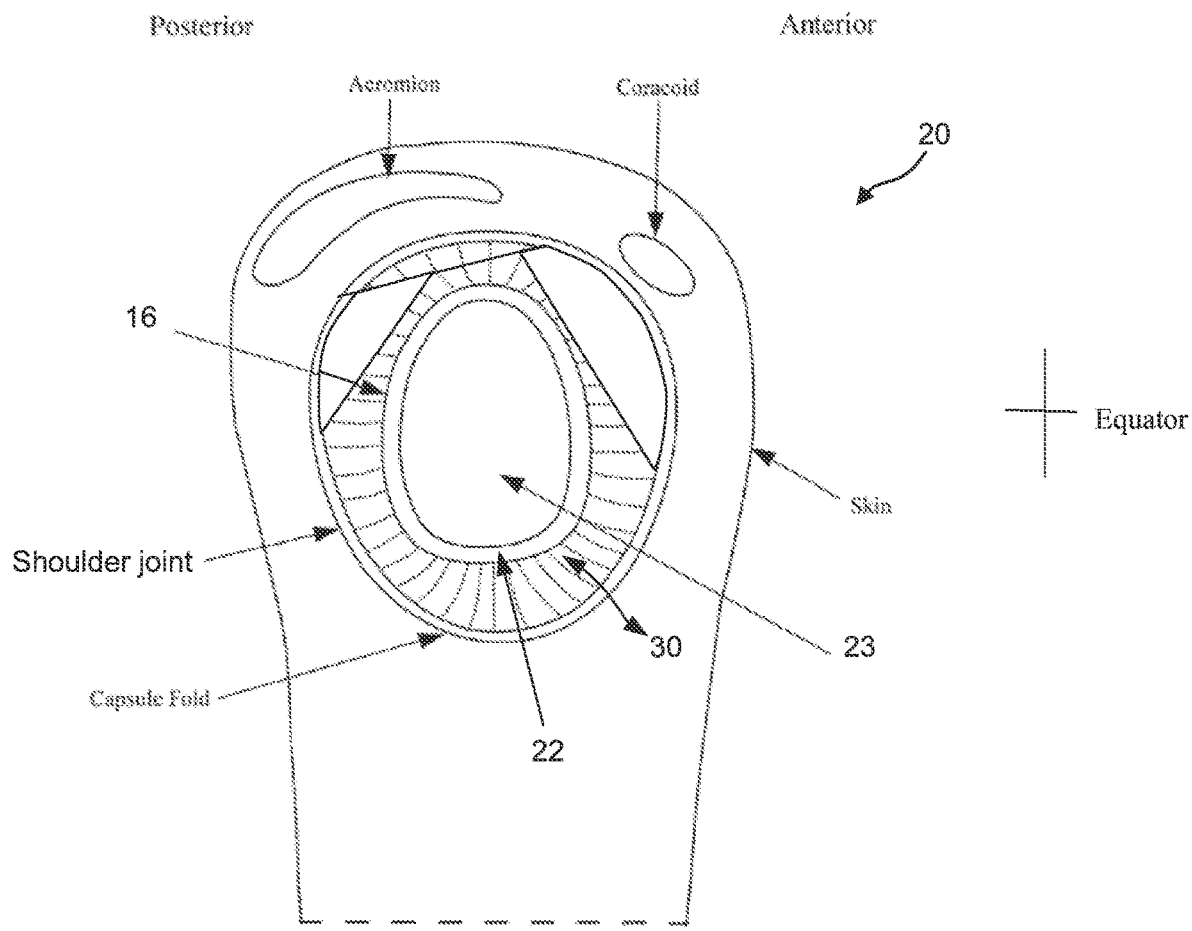
FIG. 2 is a sagittal view of a section of the human shoulder anatomy.

FIG. 2 is a sectional view of the shoulder 20 of the human anatomy showing the cavity 23 of the glenoid bone 14 and labrum 16. Such structures lie under the skin of a human shoulder 20. The shoulder 20 can be roughly divided into an upper or superior, (e.g., that portion above equator 32) and a lower or inferior portion (i.e., that portion below equator 32). The shoulder 20 can also be divided into an anterior portion (at the front of the human body) and a posterior portion (at the back of the human body).

A neurovascular zone 30, is located in the inferior portion of the shoulder. The neurovascular zone 30 is an area of nerves and vessels that travel together to innervate the shoulder joint 10.

Due to accidents, activity, or other circumstances, the shoulder joint 10 can be injured. A tear in the labrum 16 is a common injury caused by forceful twisting of the shoulder, frequently during participation in vigorous or sports activities. The labrum tear 22 produces painful instability of the shoulder joint 10. Surgery is desirable to repair the labrum tear 22 and restore stability of the shoulder joint 10 as well as prevent premature arthritis.

Repairs to a labrum tear 22 in the superior portion of the shoulder 20 are relatively straightforward because they are easily accessible without entering the neurovascular zone 30 and without suboptimal drilling of glenoid bone 14 and labrum 16. However, repairing any labrum tear 22 located at the inferior portion of the shoulder 20 is more complicated because it is adjacent to the neurovascular zone 30, and any damage to the neurovascular zone 30 could cause serious nerve damage and greatly impair the shoulder 20.

Conventional techniques to repair a labrum tear may involve the use of implants such as anchors, sutures, and other devices. To insert such implants for repair of a labrum tear, open or arthroscopic surgical techniques may be employed. The open surgical technique may be undesirable as it accesses the torn labrum through a large outside incision, which itself increases trauma to the shoulder 20. Alternatively, the arthroscopic technique accesses the shoulder joint 10 through small incisions in the shoulder 20 to insert an arthroscope (for viewing of the tear), inserting and guiding pilot hole drill, and implanting or fixing the implant. The arthroscopic technique is generally preferred since it avoids trauma associated with large outside incision(s).

Figure 3:
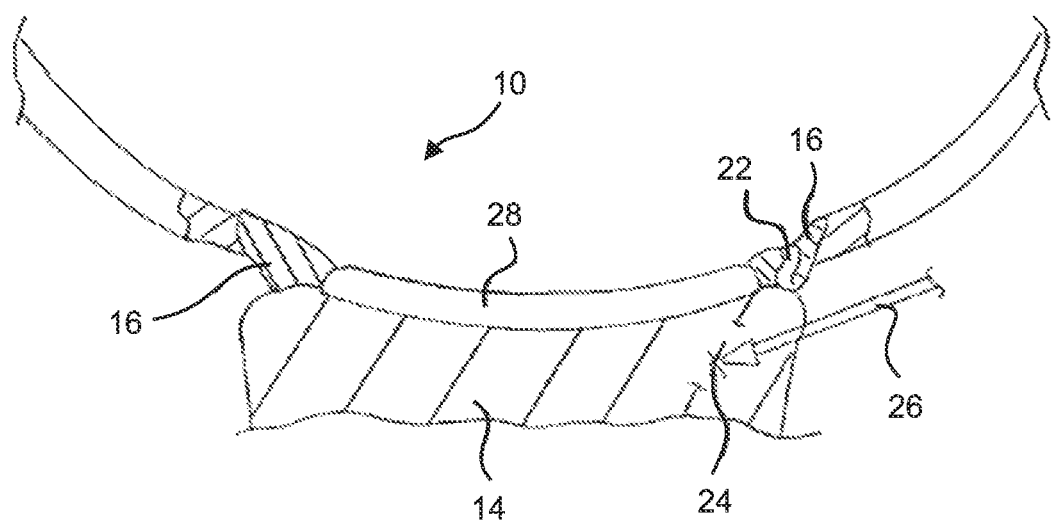
FIG. 3 is a view of a portion of the anatomy of the human shoulder as well as a potential drill site for repairing a labrum tear.

FIG. 3 illustrates a portion of the shoulder 10 with a tear 22 to the labrum 16 located in inferior portion. Typically, with the arthroscopic surgical technique, a rigid guide device is pushed up to and against the glenoid rim 28. The guide device is then held stationary against glenoid rim 28 in a desired path of a pilot hole 24. A bone drill 26 is passed through the guide device to create the pilot hole 24. The guide device remains pushed against the glenoid rim 28 and unmoved to maintain alignment until an implant is inserted in the labrum tear 22.

However, arthroscopic instruments used in the conventional techniques are limited in the range of labrum tears that can be repaired. Arthroscopic instruments are introduced into shoulder joint 10 preferably through safe portals, generally located level with or superior to the glenoid equator. An arthroscopic instrument inserted through safe portals has limited ability to align with labral tears, particularly more inferior tears. The arthroscopic instrument is usually not inserted through portals far inferior to the glenoid equator because of increased risk of nerve damage.

Thus, in attempting to repair an inferior labrum tear 22, using conventional techniques, one risks suboptimal implant alignment at the glenoid rim or risks neurovascular damage through the inferior approach to improve implant alignment at the glenoid rim.

Other problems exist with surgical techniques and instruments for shoulder joint repair. One type of conventional guide instrument is made to be rigid because it is pushed to stabilize itself against the glenoid rim 28 and maintain correct alignment of the pilot hole 24's drilling path. A flexible guide would unacceptably deform when pushed. From the onset of drilling the pilot hole 24 until insertion of a fixation implant, such rigid guide instrument must be held unmoved, pushed against the glenoid rim 28 to maintain proper alignment. If the guide instrument is moved after drilling, alignment with the pilot hole 24 may be lost, resulting in faulty or improper insertion of the fixation implant. Undesirable re-drilling may be necessary. Re-drilling in a limited space of the glenoid rim 28 increases the risk of creating overlapping or converging pilot holes and resultant failure of implant fixation.

Furthermore, an arthroscopic guide instrument inserted through a safe portal at or superior to the glenoid equator points inferiorly toward inferior labrum tear. Guide alignment with glenoid rim 28 approaches tangential as the location of the labrum tear 22 becomes more inferior, as seen in FIG. 3. With very inferior labrum tears, the guide may be aligned tangential to or even point away from the glenoid rim, thus preventing or hindering the creation of a suitable pilot hole 24.

Various rigid guide instruments may be formed angulated rather than straight in an attempt to improve alignment with the glenoid rim 28. But a high degree of angulation may be required to properly align with inferior labrum tears 22. However, it is not feasible to stabilize a highly angulated rigid instrument pushed against the glenoid rim 28. First, rather than generating the desired stabilizing compressive force, pushing a highly angulated guide into the should joint 10 produces destabilizing lateral shear force between the guide device's tip and the glenoid rim 28. Second, the drill 26 must be rigid to create an accurate drill path and pilot hole 24. A rigid drill 26 cannot pass through the bore of highly angulated rigid drill guide unless bore diameter is much larger than the diameter of the drill 26. But a large guide instrument has limited maneuverability in the confines of the shoulder joint 10.

Thus, a device and technique for repairing soft tissue and bone, such as an inferior labrum tear, utilizing safe arthroscopic portals would be a notable advance in the medical arts.

Systems and Methods for Tissue and/or Bone Repair

In accordance with embodiments of the present disclosure, systems and methods are provided for the repair of soft tissue and bone repair, which are particularly useful for labral repairs in the human shoulder. According to some embodiments, the systems and methods use a kedging line to pull and hold a guide device to repair labrum tears that are difficult to reach without suboptimal alignment with the glenoid bone and avoid the neurovascular zone (as required with pushed devices of the previous designs). The present systems and methods can employ high angulation of a guide cannula to improve its alignment at the tear while held stationary at the glenoid bone, thus, minimizing a destabilizing shear force compared to pushed devices of the conventional techniques.

Figure 4:
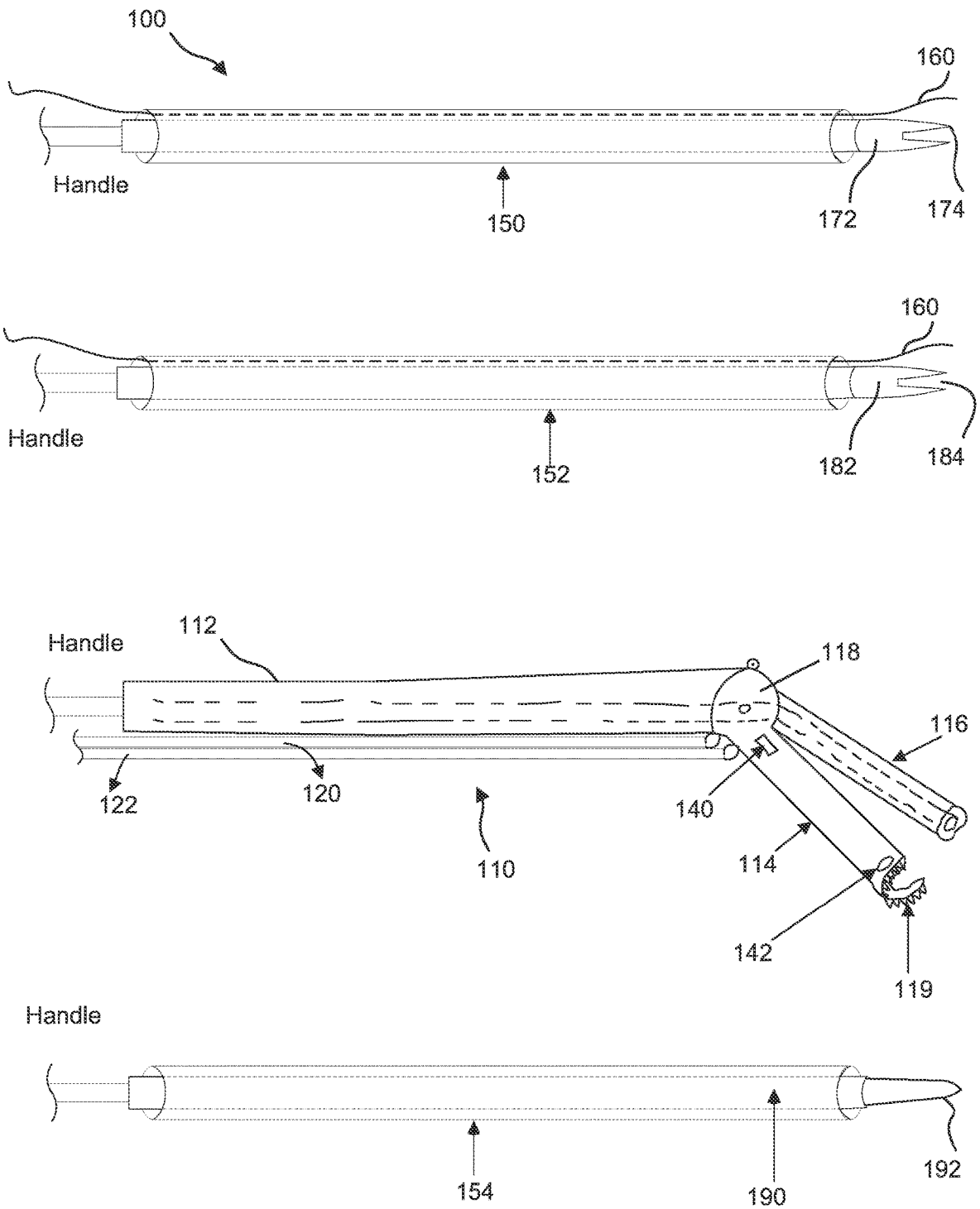
FIGS. 4 and 5a-e illustrate components of a system for soft tissue and bone repair, according to some embodiments.

FIG. 4 illustrates a system 100 for soft tissue and bone repair, according to some embodiments. The system 100 may include a guide device 110 that is used in conjunction with one or more cannulas—a guide cannula 150, a kedging line cannula 152, and a guide cannula 154.

In some embodiments, as shown, guide device 110 may itself include a proximal cannula 112, a slotted cannula 114, and a distal cannula 116. In some embodiments, proximal cannula 112 may be rotatably connected to the distal cannula 116 and the slotted cannula 114 by a hinge 118. The distal cannula 116 and the slotted cannula 114 rotate independently with respect to each other and the proximal cannula 112, as described in further detail below. Slotted cannula 114 may be open along its axial length so that distal cannula 116 can be nested within slotted cannula 114. In some embodiments, slotted cannula 114 is designed to stop further angulation of distal cannula 116 when it reaches coaxial alignment. Over angulation of the distal cannula 116 is prevented. In addition, the slotted cannula 114 contour "nests" and stabilizes the distal cannula 116, preventing its deflection from the desired plane of rotation. In some embodiments, because they share the hinge 118, slotted and distal cannulas 114 and 116 are able to rotate about the same axis. The distal cannula 116 is coaxially aligned with the slotted cannula 114 when they are at the same angulation with respect to the proximal cannula 112.

In other words, consistent with the present disclosure, the guide device 110 may include commonly hinged cannulas that can be pulled by a kedging line 160 to hold the cannulas in the desired path or alignment at the glenoid rim. The kedging line 160 may be constantly pulled— i.e., tension is applied—to maintain the guide device 110 in place and immobile at the glenoid rim 28 during drilling a pilot hole 24 into the glenoid rim and inserting an implant 192 at a site of the tear. Thus, the guide device 110 is not pushed against the glenoid rim as in conventional techniques.

In some examples, the angulation or rotation of slotted and distal cannulas 114 and 116 may be controlled by one or more respective control rods 120, 122 and/or a kedging line 160. In some examples, each control rod 120 or 122 is movably connected to proximal cannula 112, so that it can move parallel to the length of cannula 112 for controlling the angulation or rotation of slotted and distal cannulas 114 and 116. In some embodiments, guide device 110 may include one or more brake components to fix the amount of angulation or rotation for one or both of cannulas 114, 116.

In some embodiments, the slotted cannula 114 is provided with a frictional tip 119 that can be used to make secure contact with the surface a of glenoid bone 14, specifically at the glenoid rim 28. In some embodiments, frictional tip 119 may be contoured, serrated and/or textured for secure contact on the glenoid rim 28.

The one or more guide cannulas 150-154 can be used in conjunction with guide device 110 for soft tissue and bone repair including, for example, repair of a labral tear 22 located in the inferior portion of the glenoid. Guide cannulas 150-154 may be used to deliver various items into the area of surgery. As shown, such items can include a grasping device 172, 182 and a kedging line 160, which are passed through the guide cannula 150, 152. In some embodiments, the grasping device 172, 182 can be formed with pincers, hook, or snare end 174, 184 to deliver or alternately grasp or gain control of the kedging line 160. Other devices that may be delivered or passed through a guide cannula 154 can include an implant shaft 190 for delivering an implant 192.

In some examples, the guide cannula 150 and the kedging line cannula 152 may be used to introduce the kedging line 160 into the shoulder joint, for example from anterior and posterior portals, respectively. The kedging line is passed through the guide cannula 150, for example, by a first grasper 172 and is passed to a second grasper 182—which was passed through the kedging line cannula 152—situated within the glenoid cavity that withdraws it from the posterior portal.

FIGS. 5a-5e shows additional details for guide device 110.

Figure 5A:
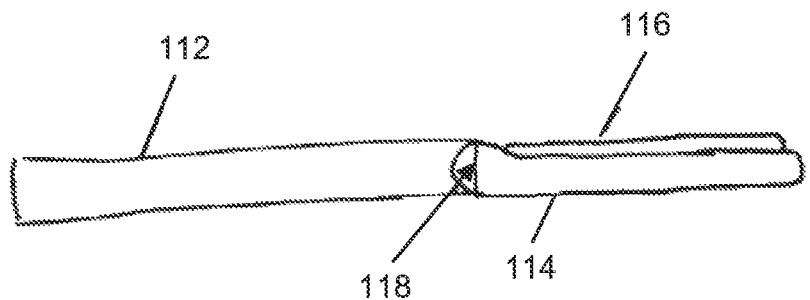
Figure 5B:
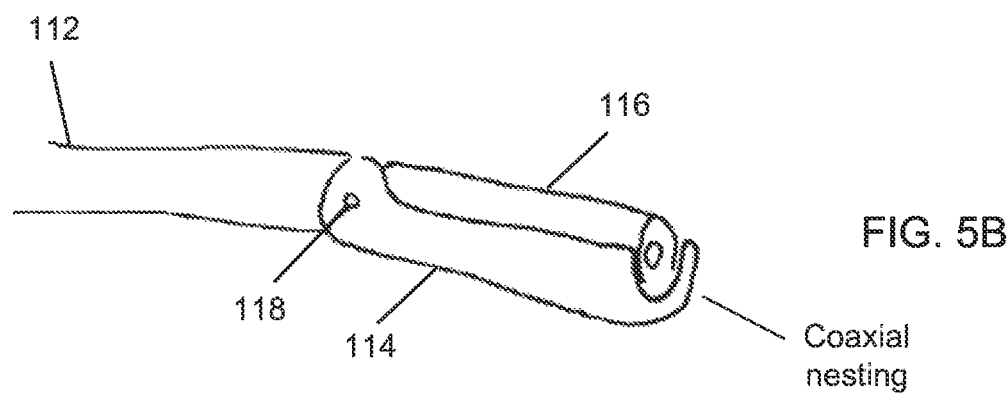

Referring to FIGS. 5a and 5b, the distal cannula 116 is nested in the slotted cannula 114, and both cannulas 114, 116 are angulated with respect to the proximal cannula 112. In some embodiments, the slotted cannula 114 is shaped and formed to prevent distal cannula 116 from angulation beyond coaxial rotation in one direction. In other words, distal cannula 116 cannot rotate through or "overshoot" the slotted cannula 114. Maximal or terminal angulation of distal cannula 116 is equal to and coaxial with slotted cannula 114. As such, slotted cannula 114 cannot be angulated less than distal cannula 116 but will be coaxial when both are at a minimum or zero degrees of angulation, parallel with proximal cannula 112.

Figure 5C:
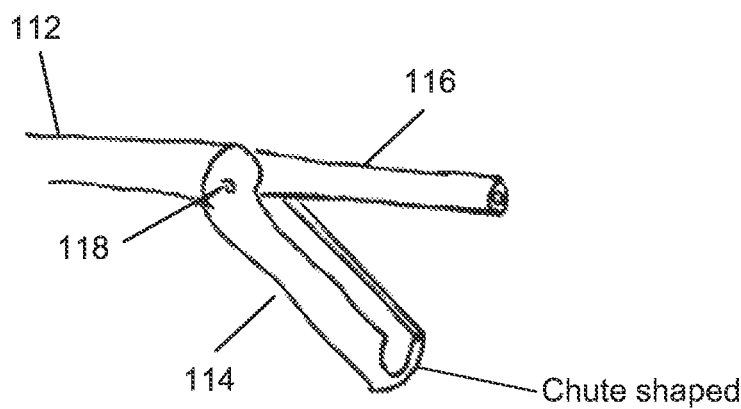

Referring to FIG. 5c, in some examples, slotted cannula 114 is chute-shaped to enable distal cannula 116 to nest within and be coaxially aligned with slotted cannula 114 when distal cannula 116 is angulated or rotated the same as the slotted cannula 114.

Figure 5D:
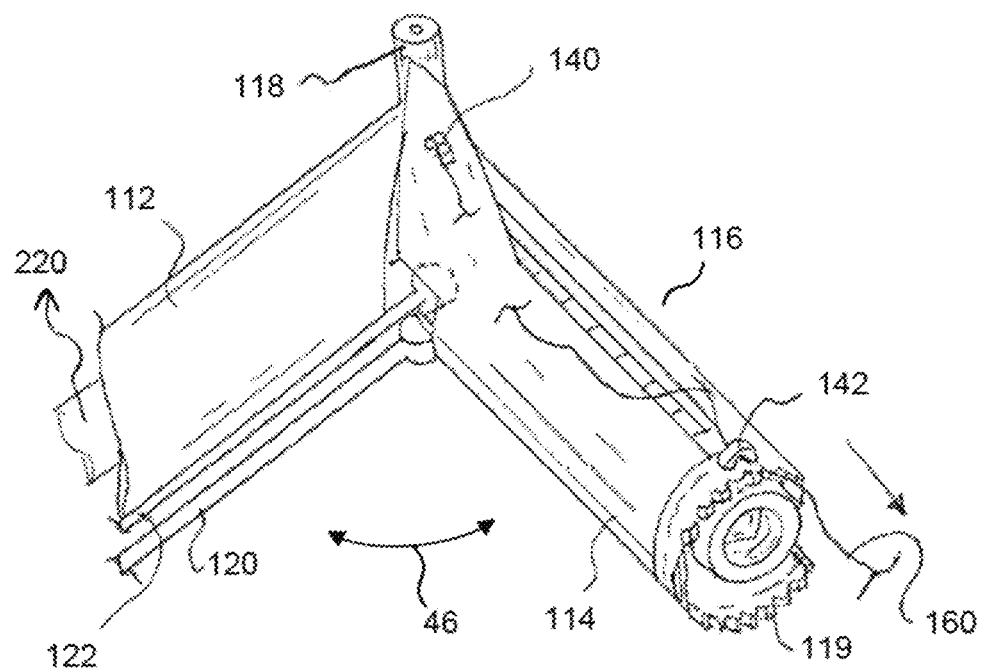
Figure 5E:
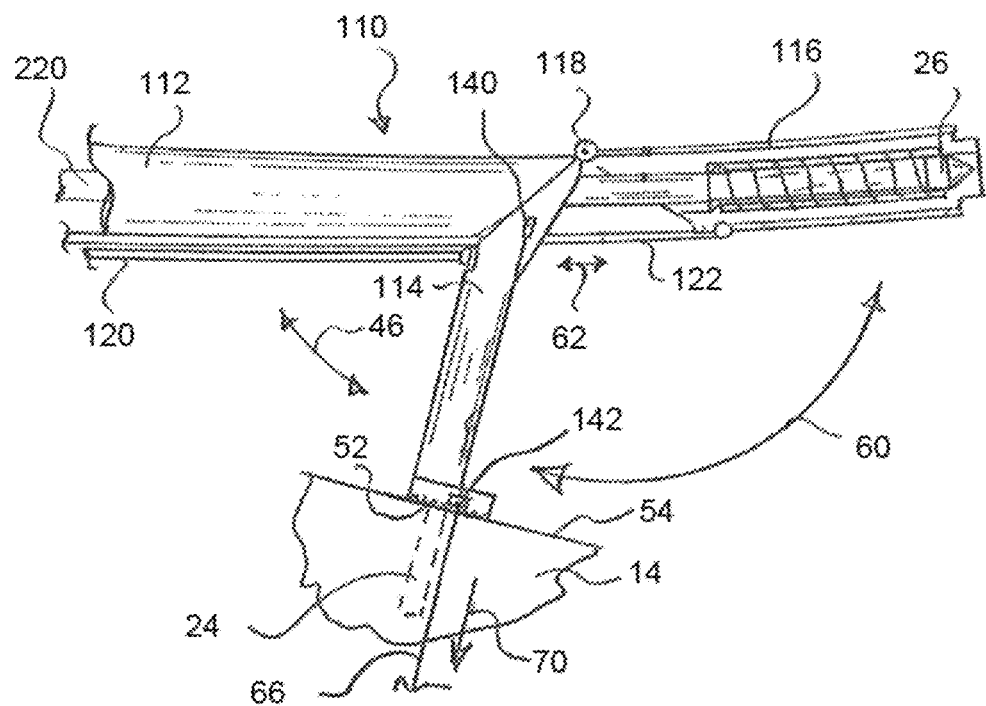

With reference to FIGS. 5d and 5e, in some embodiments, the proximal cannula 112 and distal cannula 116 may be formed and sized to allow passage of a drill 26 and/or implant. The drill 26 may include a drill head 210 connected to flexible shaft 220, which may be used to move and/or power the drill head 210. The implant 192 may be implanted at or proximate a labral tear 22 for repairing same. The size of proximal and distal cannulas 112, 116 are preferably no larger than necessary in order to allow of passage, e.g., of the drill 26 and/or implant, thereby minimizing the profiles of the proximal cannula 112 and distal cannula 116. Distal cannula 116 can be formed shorter than slotted cannula 114 so that even when the frictional tip 119 of the slotted cannula 114 is held against a glenoid rim 28, distal cannula 114 is free to rotate about hinge 118 without interference from the glenoid rim 28.

In some embodiments, slotted cannula control rod 120 may be operated (e.g., pushed, pulled, and/or rotated) to angulate, rotate, or extend the slotted cannula 114, for example, with respect to proximal cannula 112. In some embodiments, distal cannula control rod 122 may be operated (e.g., pushed, pulled, and/or rotated) to angulate, rotate, or extend the distal cannula 116, for example, also with respect to proximal cannula 112. In some embodiments, movement of control rod 122 may be linear or non-linear to affect a smooth and controlled rotation of distal cannula 114 relative to proximal cannula 112.

Guide device 110 may also include or be provided with a kedging line attachment 140 and a guide 142. In some embodiments, the kedging line attachment 140 and guide 142 may be attached or formed on slotted cannula 114. The kedging line attachment 140 can serve as an anchor to pull the kedging line 160. In some examples, the kedging line attachment 140 is ring-shaped. The guide 142 is used to guide or direct the kedging line 160 at the distal end of guide device 110. In some examples, the guide 142 is located at the tip of the slotted cannula 114. In some examples, the kedging line attachment 140 is located on the slotted cannula 114 at the end proximate the hinge 118. The guide 142 and the kedging line attachment 140 are positioned such that the slotted cannula 114 does not veer at its tip or end, from the desired line path. The kedging line 160 may be passed through the guide 142 and attached or coupled to the kedging line attachment 140. Pulling of kedging line 160, for example, by a surgeon during an operation, can guide or direct the slotted cannula 114 and drilling cannula 116 towards the desired drilling path or location.

Figure 6:
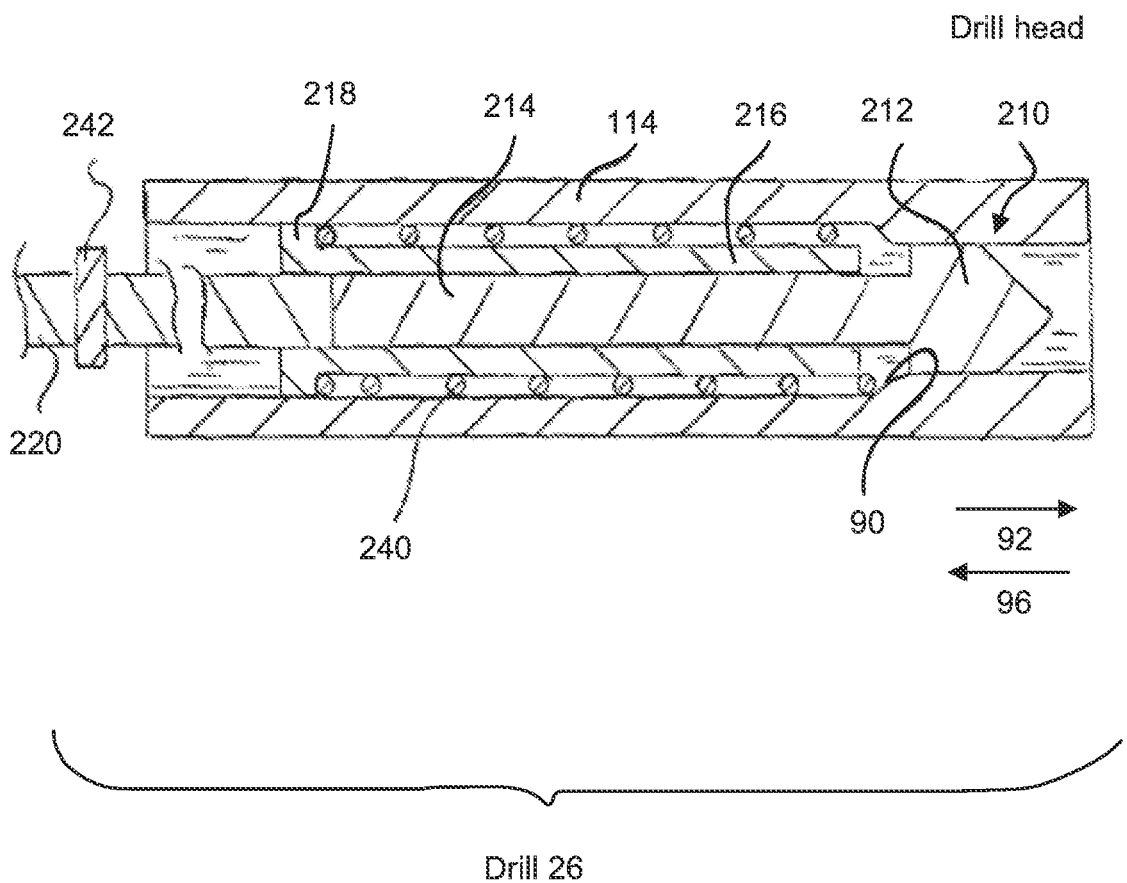
FIG. 6 is a sectional view of a portion of the guide cannula, according to some embodiments.

FIG. 6 is another view of portions of guide device 110, in partial cross-section to show drill 26 within distal cannula 116. The drill 26 comprises drill head 210 coupled to drill shaft 220, which are inserted in the guide device 110. The drill shaft 220 is flexible, and thus capable of bending as the distal cannula 116 may be rotated to drill the pilot hole 24 in glenoid bone 14. The drill shaft 220 can function even when the distal cannula 116 is angulated or rotated with respect to the proximal cannula 112.

The drill head 210 includes a bit 212 and a shank 214 movably inserted in a sleeve 216 having a flange 218. In some embodiments, shank 214 may have a smaller diameter than drill bit 212. The drill shaft 220, which may provide power for the drill head 210, is connected or attached to the drill head 210 at one end of shank 214. In some embodiments, the shank 214 may have the same diameter as the drill shaft 220. Bit 212 can be a rigid cutting bit which is located at the other end of the shank 214.

Shank 214 is slidable within sleeve 216. Sleeve 216 itself is movable or slidable within distal cannula 116. In some embodiments, a coil spring 240 may be located between the sleeve 216 and the interior of cannula 116. As sleeve 216 is moved within cannula 116, e.g., to advance drill bit 212 beyond the end of the distal cannula, the coil spring 240 is compressed against an inner shoulder of the cannula 116 by flange 218. The distance that drill bit 212 can travel or move beyond the end of distal cannula 116 may be limited by a collar 242 (mounted or formed on shank 214) when it contacts the shank 214. In this way, excessive drilling by bit 212 can be prevented.

Other embodiments for drill 26 are possible, as would be understood by one of ordinary skill in the art.

Operation

The systems and methods of the present disclosure provide advantages over conventional techniques. According to some embodiments, the systems and methods may be used to direct or move the drill 26 to a hard-to-reach location in the anatomy (e.g., proximate a labral tear 22 in the inferior portion of the glenoid) with less damage to the patient than prior art techniques. Furthermore, the systems and methods can then ensure that the alignment of the drilling path and the position of the surgical device are preserved from the onset of drilling a pilot hole 24 into the glenoid bone 24 until completion of insertion of the implant. This can be accomplished through a kedging operation.

Kedging is a technique of applying a pulling force on an object by means of an attached line (e.g., kedging line 160) to move or advance the object (e.g., the distal end of guide device 110) to the desired location. When the kedging line is pulled tight, it forms a straight line, the shortest distance between two points. The object will be pulled in the straight path of a taut kedging line 160 toward the source of the pulling force (which may be applied by a surgeon during operation).

The method of operation for the systems of the present disclosure (including guide device 110) are shown in FIGS. 7a-7l. In some embodiments, the systems and methods use or employ a kedging technique (e.g., with kedging line 160) in surgery to make a repair at a difficult-to-reach site (e.g., a labrum tear 22 located in the inferior portion of the glenoid).

Figure 7A:
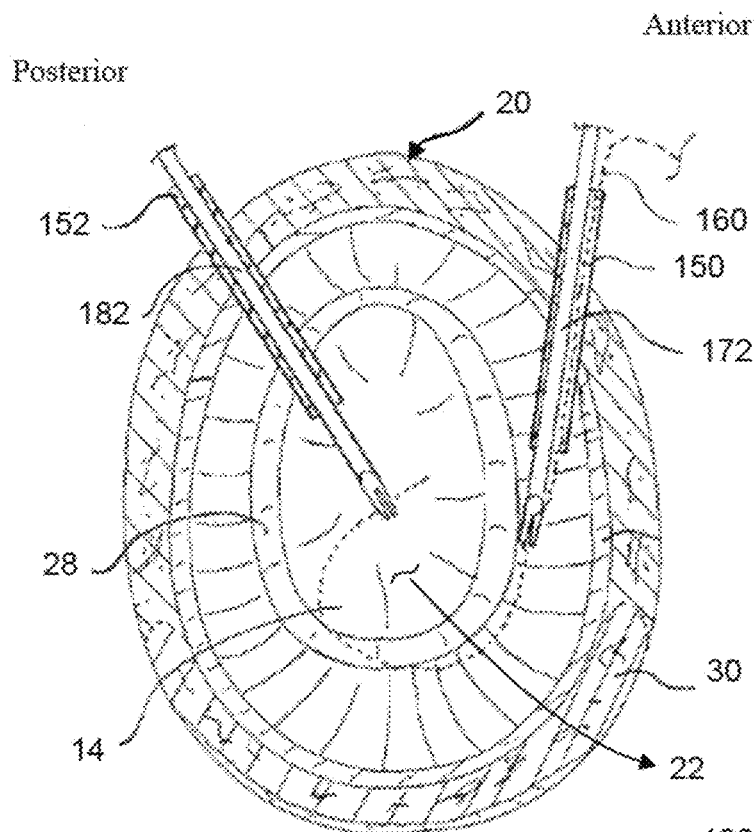

Referring to FIG. 7a, first and second cannulas 150, 152 are inserted, for example by a surgeon or operator, into the shoulder 20 through incisions safely made in the superior portion— i.e., away from the neurovascular zone 30. As shown, one incision is at the posterior and another incision is at the anterior. Grasping devices 172, 182 are inserted into the cannulas 150, 152 in order to deliver and pass a kedging line 160 within the shoulder 20 from one of the anterior or posterior incision points to the other of the anterior or posterior incision points. In some examples, grasping devices 172, 182 may be operated by the surgeon or operator using their handles that remain outside the shoulder 20. The grasping devices 172, 182 are used to maneuver the kedging line 160 within the shoulder joint. Cannulas 150, 152 serve as guides, respectively, for grasping devices 172, 182 for the maneuvering. In some examples, the kedging line 160 is passed from grasping device 150 to the grasping device 152. The grasper 182 is then withdrawn from the cannula 152 so that the kedging line 160 is pulled out through the posterior incision point. In some examples, posterior or anterior region of the shoulder may not be available, thus, the kedging technique may be adapted for other regions in accordance with the teaching of the present disclosure.

Figure 7B:
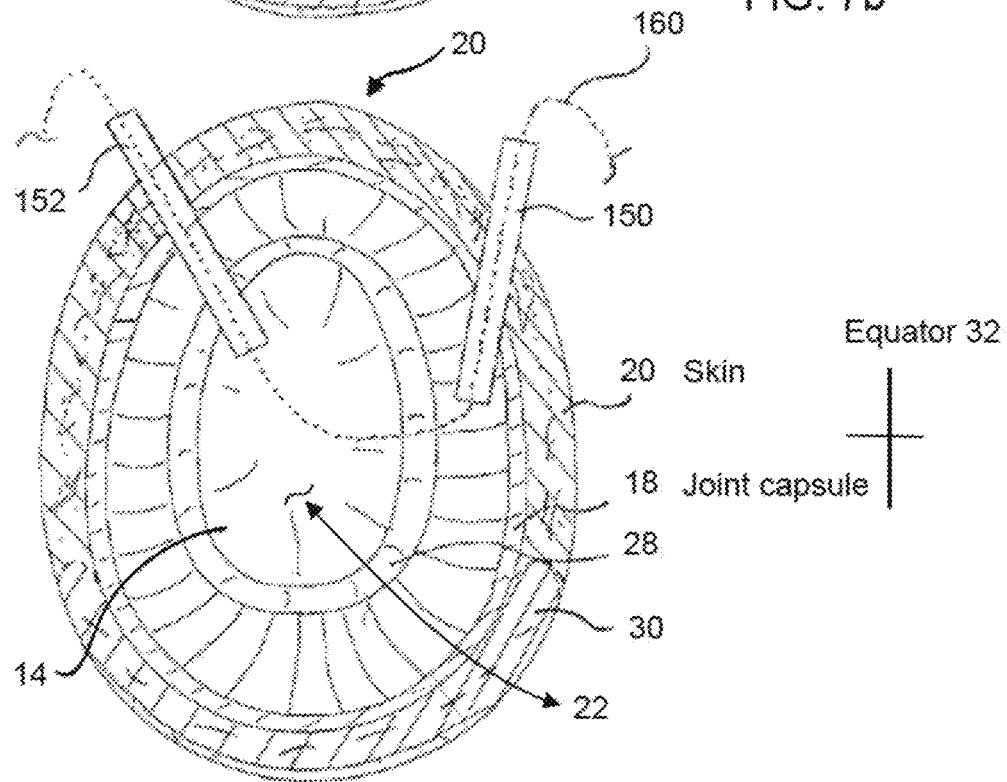

Referring to FIG. 7b, grasping devices 172, 182 have been removed from the respective cannulas 150, 152 and the kedging line 160 now extends from cannula 150, through the shoulder to cannula 152, such that both ends of kedging line 160 lie outside the shoulder. One end of kedging line 160 may be attached to the guide device 110, for example, at kedging line attachment 140, and routed through guide 142 of the slotted cannula 114.

According to some embodiments, the kedging technique may be adapted or employed for situations where the posterior or anterior aspect of a shoulder is not available as a safe portal.

Figure 7C:
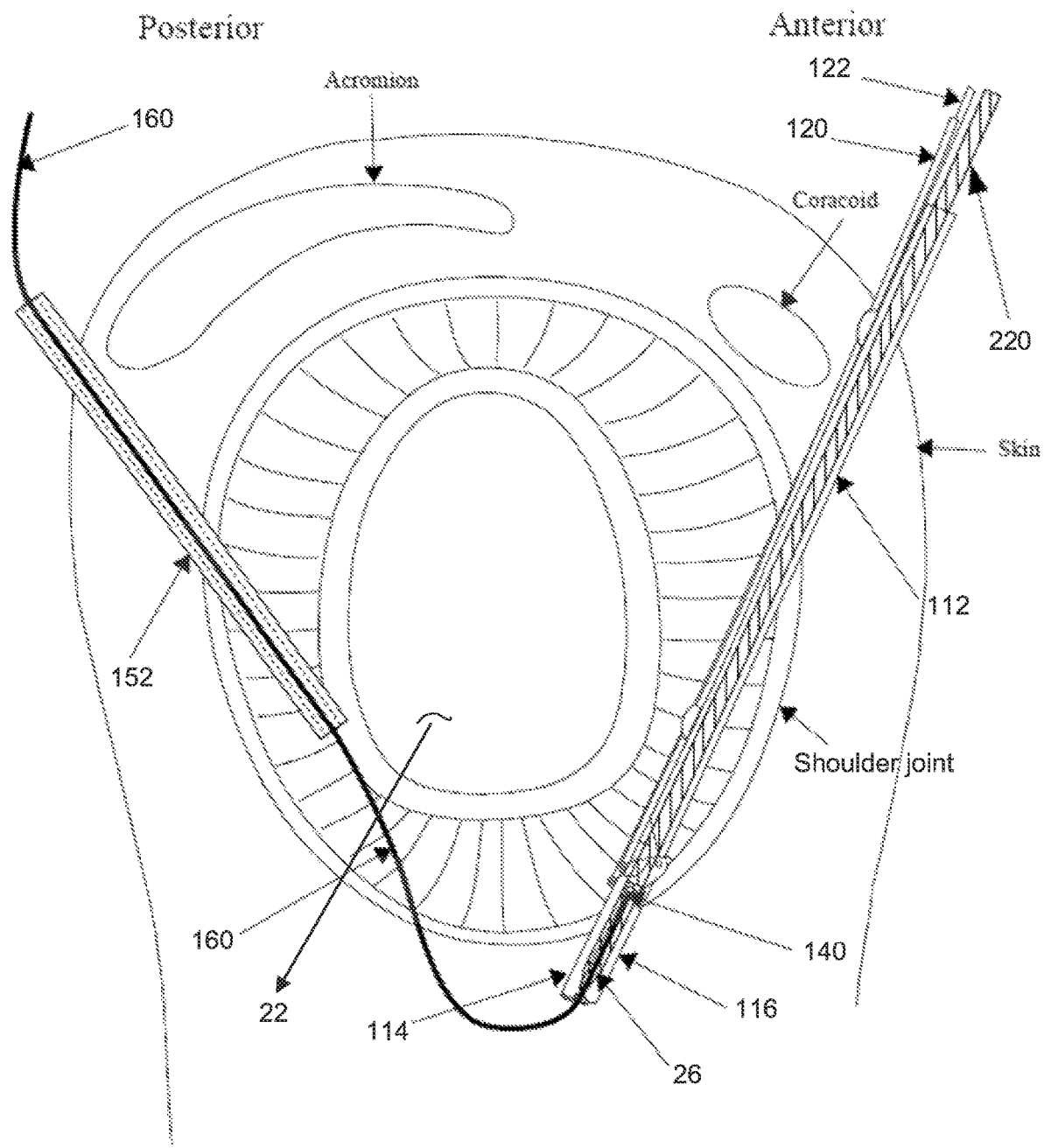

Referring to FIG. 7c, the guide device 110, with attached kedging line 160, is inserted into the shoulder 20 through guide cannula 150. In some examples, the guide device 110 may be inserted into the anterior portal— and follow the kedging line 160 into the shoulder joint—as the kedging line 160 is pulled from the posterior portal.

In some examples, the guide device 110 may be positioned in the non-angulated state before insertion. That is, the guide device 110 may be inserted into the shoulder joint when the slotted cannula 114 and the nested distal cannula 116 are parallel and coaxially aligned with the proximal cannula 112. In some examples, the kedging line 160 is attached or coupled to the guide device 110, for example at the slotted cannula 114. In some examples, the guide device 110 may be loaded or contain drill 26 before it is inserted into the shoulder. The surgeon or operator may manipulate the guide device 110 using kedging line 160 so that it passes through the guide cannula 152 to the inferior portion of the shoulder, closer to the labral tear 22 to be repaired. Still the drill 26 may not be close enough to the tear for making the repair.

According to some embodiments, the kedging technique may be adapted for cases where the posterior or anterior aspect of a shoulder is not available as a safe portal.

Also, a rigid drill bit has limited elasticity and cannot be passed through a highly angulated cannula. Such a cannula would require an enlarged bore or inner circumference to accommodate a rigid drill bit. Thus, the bulkiness of the angulated cannula with the enlarged bore would interfere with the maneuverability of a surgical device in the shoulder joint 18. Alternately, a flexible drill bit could pass through a highly angulated cannula but could not reliably follow a true drill path. Thus, guide devices of the prior arts are limited to mild angulations.

The systems and methods of the present disclosure overcome or address these problems.

Figure 7D:
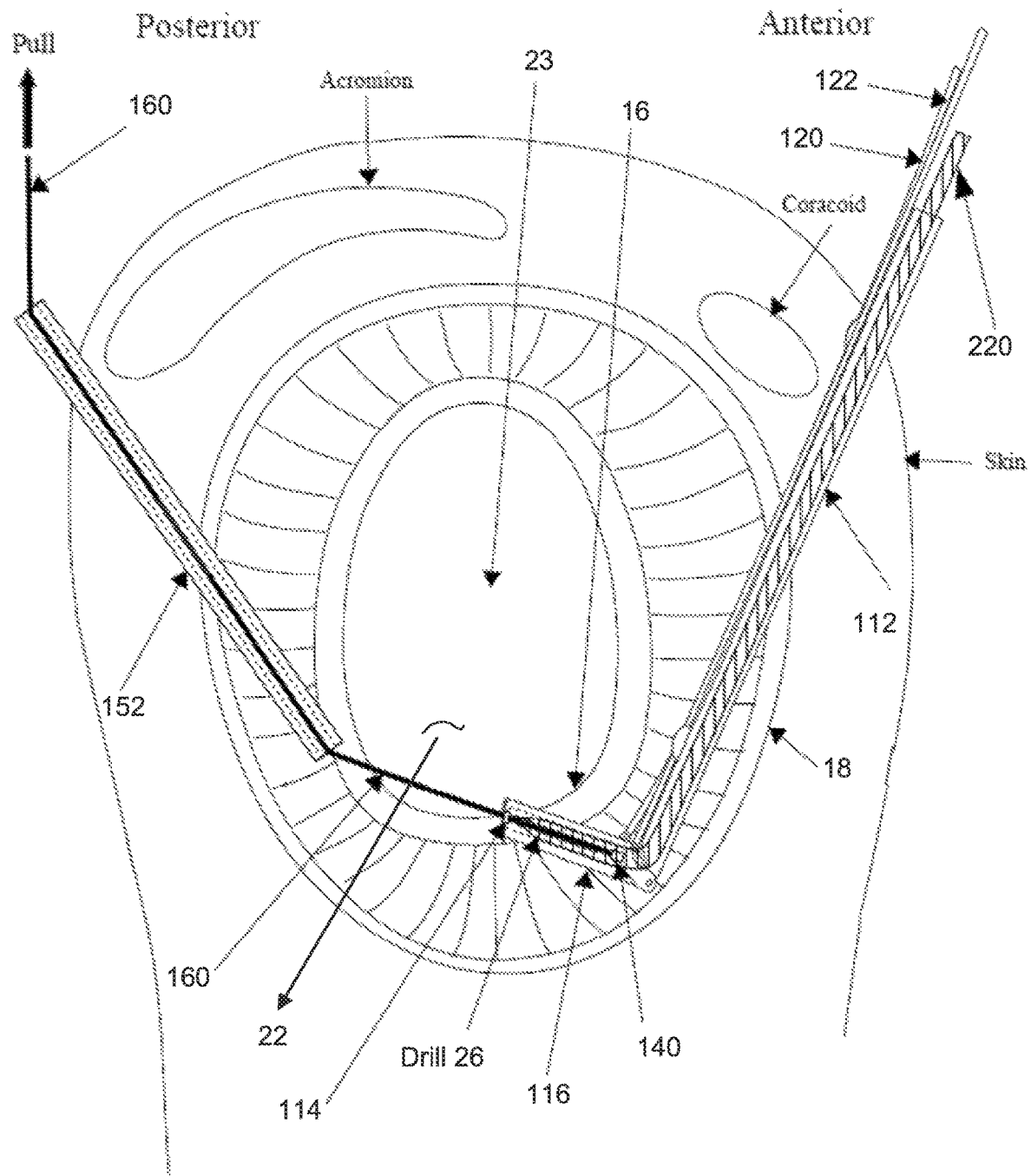

Referring to FIG. 7d, the slotted and distal cannulas 114, 116 of the guide device 110 may be rotated around hinge 118, for example, using one or more of control rods 120, 122 and pulling on kedging line 160, so that the end of guide device 110 is facing or directed towards the labral tear 22.

Kedging line 160 may be further pulled (e.g., through cannula 152) to move the guide device 110 closer towards the tear 22, thereby bringing the drill 200 contained within guide device 110 to a desirable position where it can be employed for drilling a pilot hole 24 for use in repair. That is, the drilling path for drilling the pilot hole 24 is established by the pulling kedging line 160, and in some examples, adjusting the angulation of the slotted cannula 114 and distal cannula 116. In some embodiments, when kedging line 160 is pulled tight, it forms a straight path between the source of the pull (at the end of cannula 152) and kedging line attachment 140. The path of kedging line 160 may align with the desired drilling path. Guide 152 directs the pulling force of kedging line 160 at the tip of the slotted cannula 114 so that it is moved toward and remains on the desired line path for drilling.

If the slotted cannula 114, distal cannula 116 require a redirection, the pull or tension on the kedging line 160 can relaxed and re-applied until the cannulas 114, 116 are aligned with the desired drilling path. Then, the kedging line 160 is again pulled to move or rotate the slotted cannula 114 towards the desired drilling path—at the glenoid rim 28. The slotted cannula 114 can be held in the desired drilling path by the continued pull or tension on the kedging line 160. In some embodiments, the kedging line attachment 140 and guide 142 keep slotted cannula 114 aligned to the path of the kedging line 160. In some examples, the path for the kedging line 160 is determined by the location of the tip of the kedging line cannula 152 and is independent of the orientation and shape of the kedging line cannula 152, and the location of the entry portals as a whole. In some cases, the path of the kedging line 140 and the drill path may be slightly divergent, but the stability of slotted cannula 114 is preserved by the pulling forces from kedging line 160.

As further shown in FIG. 7d, the distal cannula 116 nested with the drill shaft 220 of drill 26 is angulated or rotated, for example by the distal cannula control rod 122, until nested within and coaxial with the slotted cannula 114 to be aligned with the desired drilling path. The taut kedging line 160 provides the drill shaft 220 a proper angle to access the site of the labrum tear 22. The drill shaft 220 and drill head 210 may be oriented or positioned in the direction of the desired drilling path—to drill the pilot hole 24 in the glenoid bone 14 at a proper point of entry. Once the proper point of entry is determined, the kedging line 160 is further tightened or pulled such that frictional tip 119 is engaged into the glenoid bone 14 securing the position of the slotted cannula 114 at the glenoid bone 14. This generates stabilizing compressive pulling force at the surface of the glenoid rim. Thus, any slippage of slotted cannula 114 is avoided. The slotted cannula aligned and pulled in the direction of the desired drilling path generates a minimal destabilizing lateral shear force compared to that produced by pushing an angulated guide device as in conventional surgery techniques.

The angulations of slotted cannula 114 and distal cannula 116 are locked, for example by slotted cannula control rod 120 and distal cannula control rod 122, respectively, prior to drilling. At this point, the slotted cannula 114 is pressed against the surface of the glenoid bone 14.

Figure 7E:
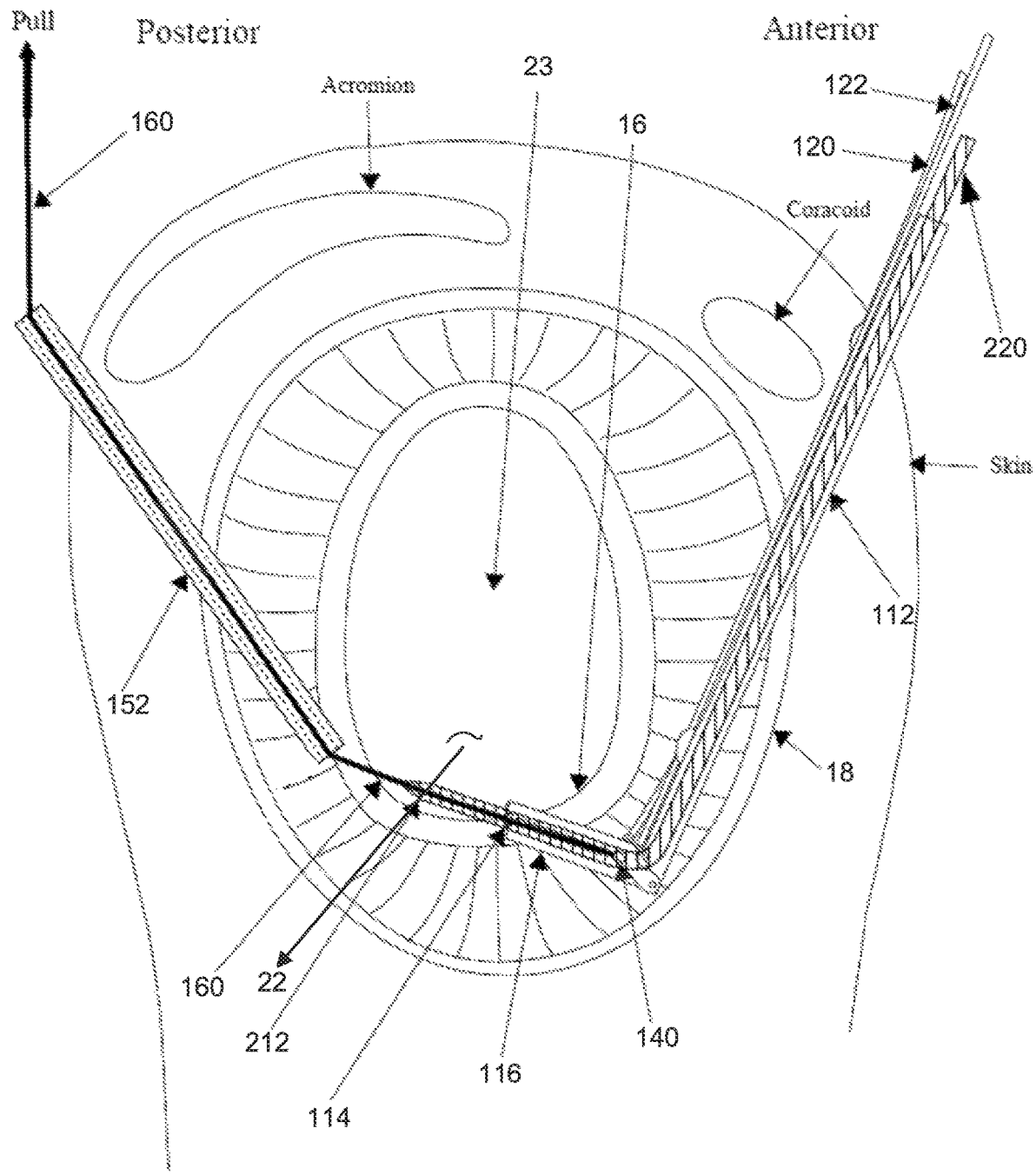

Referring to FIG. 7e, the drill shaft 220—attached with the drill 26—is advanced through and extended beyond the slotted cannula 114, such that drill bit 212 lies against surface 54 of glenoid bone 14. The slotted cannula 40 directs the drill bit 212 in the direction of the desired drilling path. At this point, the drill bit 212 drills the pilot hole 24 into the glenoid bone 14 as the drill bit 212 is advanced and extend through the glenoid bone 14.

With reference also to FIG. 6, as drill head 210 is advanced outside sleeve 216, as shown by the directional arrow 92, drill bit 212 advances or extends beyond distal cannula 116 until it reaches the surface of glenoid bone 14 as seen with reference to FIG. 7e. The sliding of the sleeve 216 relative to the drill shank 214 permits the telescoping of the drill bit 212 from the distal cannula 116. At this point, the drill bit 212 is rotated, in the direction of the directional arrow 92, to form pilot hole 24 in glenoid bone 14 near glenoid rim 28. In some examples, the drill bit 212 may be operated by an electrical instrument. In some embodiments, telescoping the sleeve 216 extends support for the drill bit 212 beyond the tip of distal cannula 116. The travel or movement of the drill head 212 is limited by the compression of coil spring 240 between drill flange 218 and distal cannula 116. The drill bit 212 is then retracted in the direction of the directional arrow 96, leaving the pilot hole 24 at glenoid bone 14. The expansion of the coil spring 240 facilitates the retraction.

Referring to FIG. 7e, the slotted cannula 114 has been angulated outwardly with respect to proximal cannula 112 the same as the distal cannula 116. As seen in FIG. 7c, the kedging line 160 is initially slack—i.e., there is no tension or pull on the kedging line 160—but the kedging line 160 is pulled taut in FIGS. 7d, 7e.

It may be apparent to those skilled in the art that the drill bit 212 may pass through the guide device 110 even if the distal cannula 116 is slightly angulated or rotated from the proximal cannula 114. However, after a certain degree of angulation between the distal cannula 114 and the proximal cannula 116, the drill bit 212 may not be able to pass through the guide device 110.

The drill bit 212 is advanced within the guide cannula and positioned within the distal cannula 114 beyond the hinge between the proximal and distal cannulas 112, 116. Only the flexible drill shaft 220 is subject to and can pass through angulation between the proximal and distal cannulas. The drill head 210 is advanced by pushing on the drill powering the drill shaft. After the pilot hole is drilled, the drill head 210 is retracted by pulling back on the drill shaft. Thus, advancement and retraction of the drill bit 212 is not restricted in producing the pilot hole 24. The angulation of distal cannula 116 with respect to the proximal cannula 112 is eliminated when returned to the non-angulated, coaxial position. Then the rigid drill can be passed out of the entire guide to be replaced by the implant and its insertion shaft. In theory, the position of the proximal cannula 112 might be slightly altered if otherwise unable to achieve coaxial alignment with the proximal cannula 112 after pilot hole 24 is drilled. If constant pull is maintained on the kedging line 160 which directly is attached to the slotted cannula 114, alignment of the slotted cannula 114 which determines drill insertion path, is not altered. In practice, the proximal and slotted cannula positions are to remain unchanged once the guide is placed in the desired position. In other words, pull on the kedging line 160 is continued without slack, to maintain guide alignment while the drill is removed and the implant at the end of its shaft is passed into the guide cannula and inserted into the pilot hole 24.

After drilling the pilot hole, the drill shaft 220 should be exchanged with the implant shaft 190. The drill bit 212 cannot be extracted or withdrawn from the distal cannula 116 when the distal cannula 116 is angulated beyond a certain degree from the proximal cannula 112. Thus, the distal cannula 116 should be moved off the glenoid bone 14 and straightened with respect to the proximal cannula 112 in order for the drill bit 212 and drill shaft 220 to be withdrawn from the guide device 110 and be exchanged with the implant shaft 190. Thus, distal cannula 116 is re-angulated and returned to coaxial alignment with respect to the proximal cannula 112 as seen in FIGS. 7f-7h.

Figure 7F:
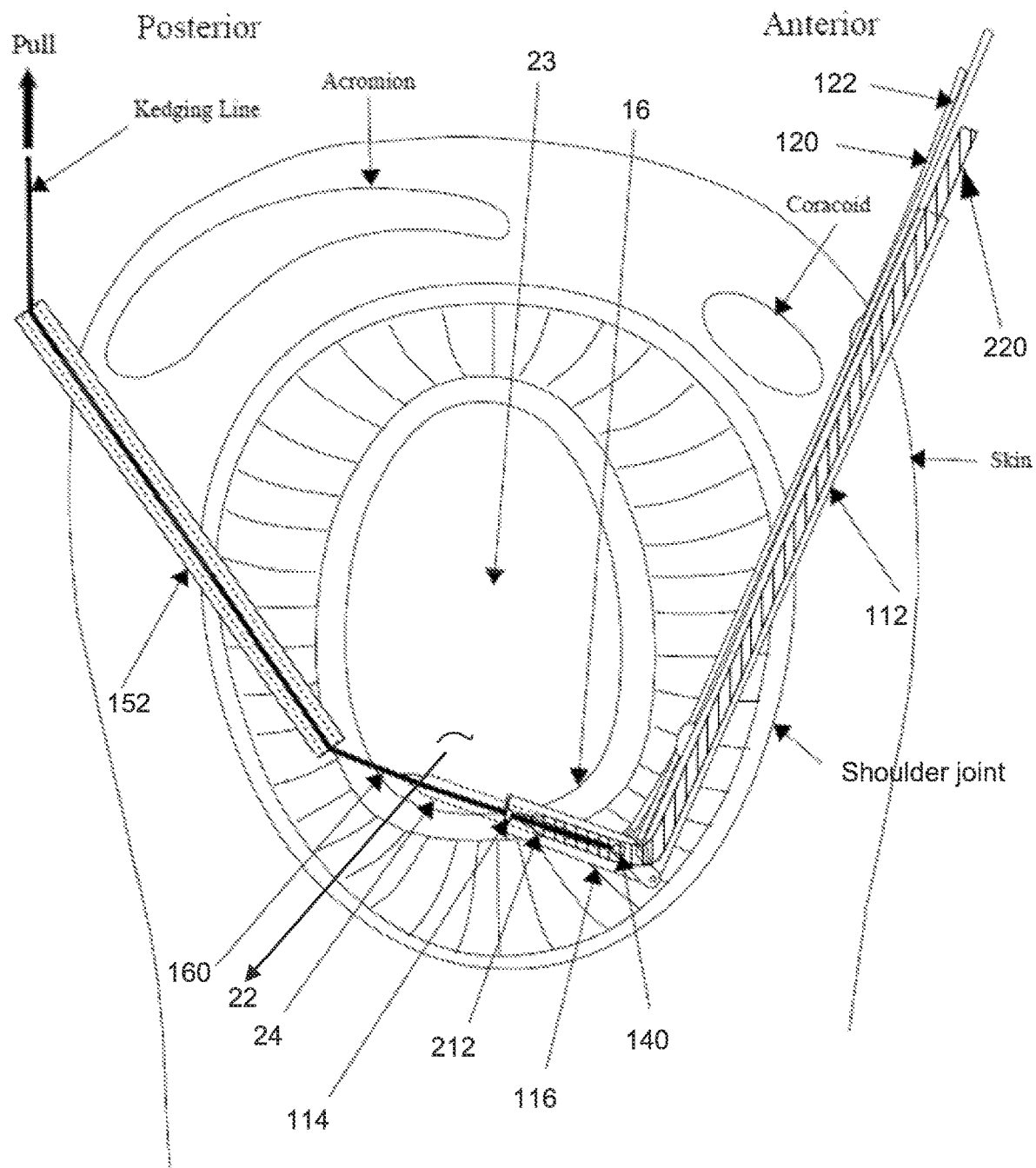

Referring to FIG. 7f, the drill shaft 220 and the drill 26 are retracted from the glenoid bone 14 back into the distal cannula 116. In some embodiments, the drill 26 is retracted from the pilot hole 24 into the distal cannula 116 before the distal cannula 116 can be rotated into coaxial alignment with the proximal cannula 112. Otherwise, the drill still located in the pilot hole 24 would prevent change of angulation of distal cannula 116. The sleeve 216—such as that described with respect to FIG. 6—self-retracts as the drill bit 212 withdraws from the pilot hole 24. The coil spring 240 is compressed during the drilling procedure and aids in the retraction of the drill 26 back into the distal cannula 116.

It is preferable that the pilot hole 24 be more perpendicular than tangential to the glenoid rim 22 at the repair site. However, in some cases, a perpendicular pilot hole on glenoid bone 14 may not be attainable and the pilot hole 24 may be oblique to the glenoid rim 22. However, in some examples, even a pilot hole with an oblique angularity is sufficient to secure a repair implant as discussed herein. The kedging line 160 can be constantly being pulled or tensioned during this procedure—and in conjunction with frictional tip 119—to secure the position of the slotted cannula 114 on the glenoid rim 22. Thus, access to the pilot hole 24 and the labrum tear 22 is not lost between the establishment of pilot hole 24 and the insertion of an implant 192.

Figure 7G:
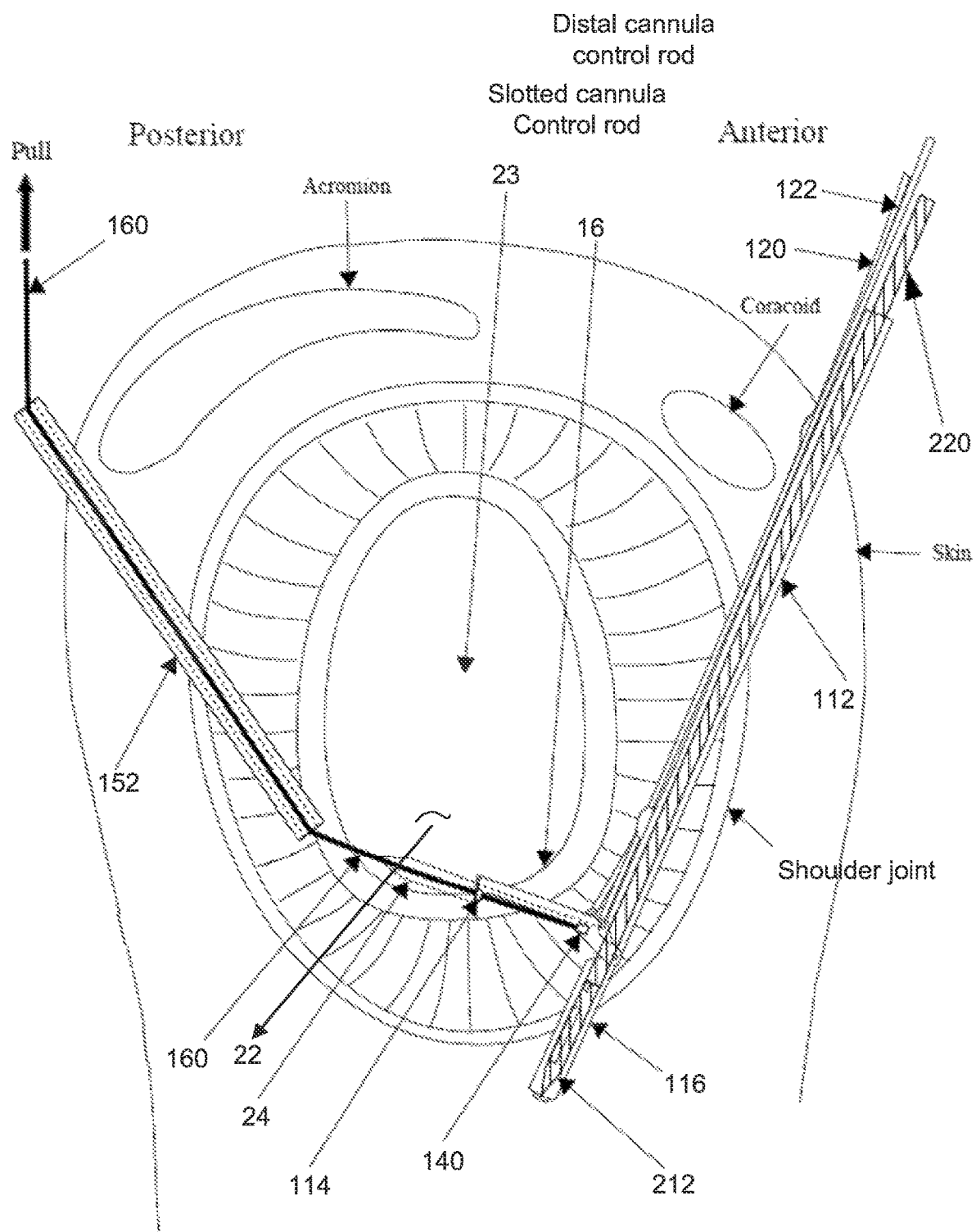
Figure 7H:
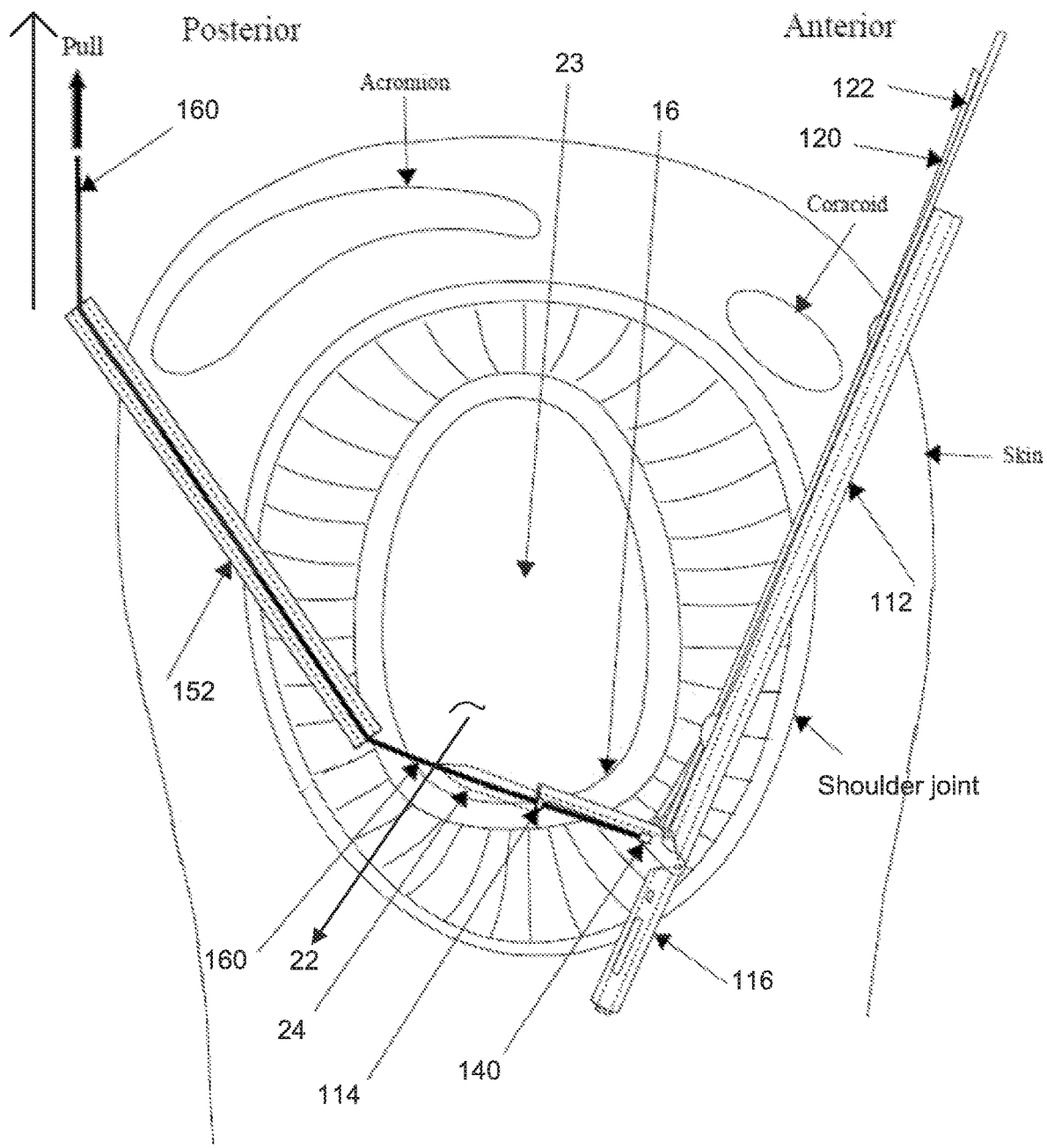

Referring to FIG. 7g, the lock on the distal cannula 116 is released and the distal cannula 116 is rotated or extended, for example by the distal cannula control rod 122, until the distal cannula 116 is coaxially straightened and aligned with the proximal cannula 112.

Referring to FIG. 7h, the drill shaft 220 and drill 26 are removed from the guide device 110. In some examples, the tension or pulling force on the kedging line 160 must be constantly maintained once the slotted cannula 114 is secured at the glenoid bone 14. The tension or pulling force on the kedging line 160 is not released until after the implant 192 is solidly fixed at the site of the labrum tear 22.

Figure 7I:
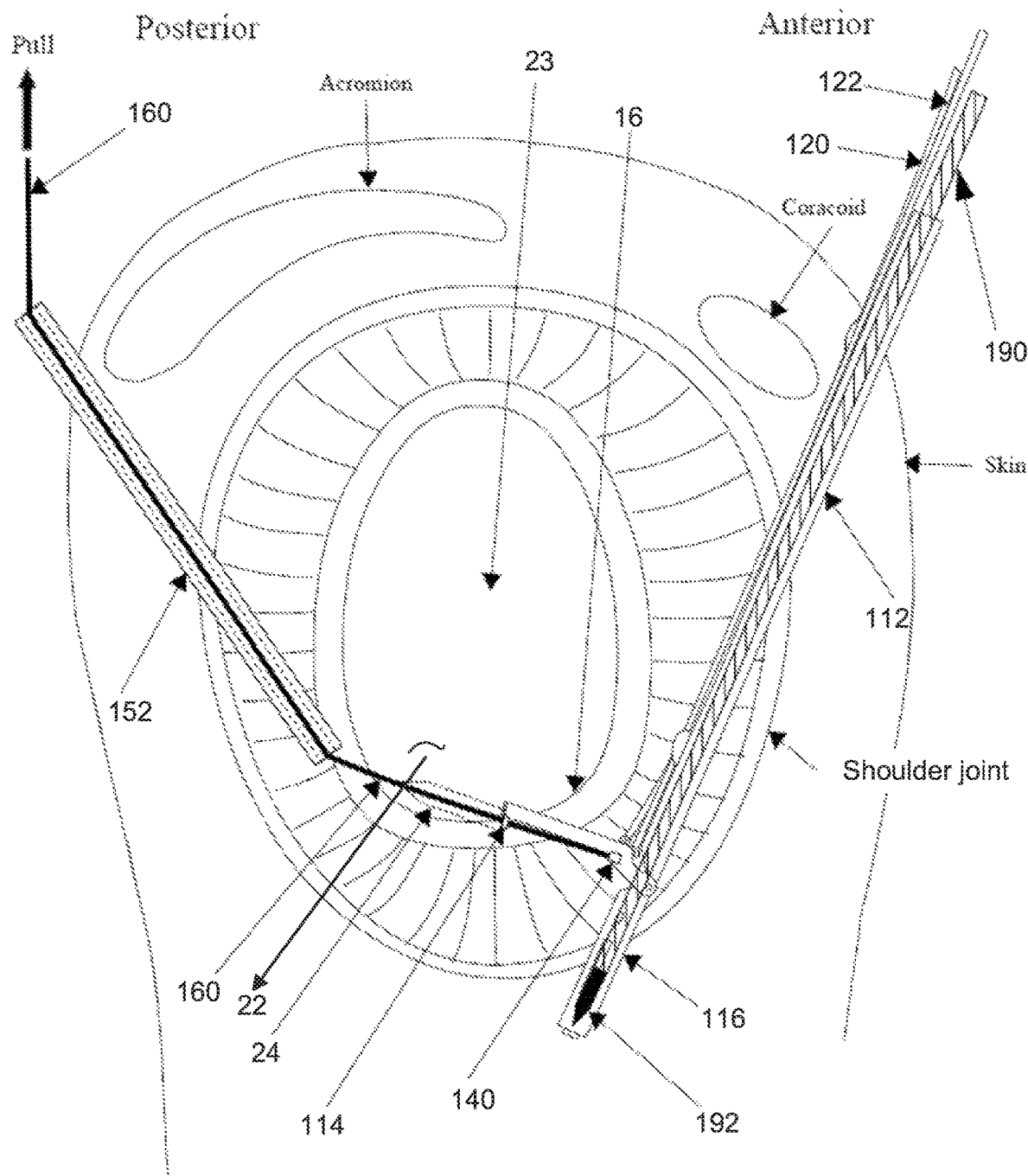

Referring to FIG. 7i, an extended or straightened implant shaft 190 attached with the implant 192 is passed through the proximal cannula 112 and distal cannula 116. The implant shaft 190 similar to the drill shaft 220 is flexible and can bend to follow the angulation of the distal cannula 116.

Figure 7J:
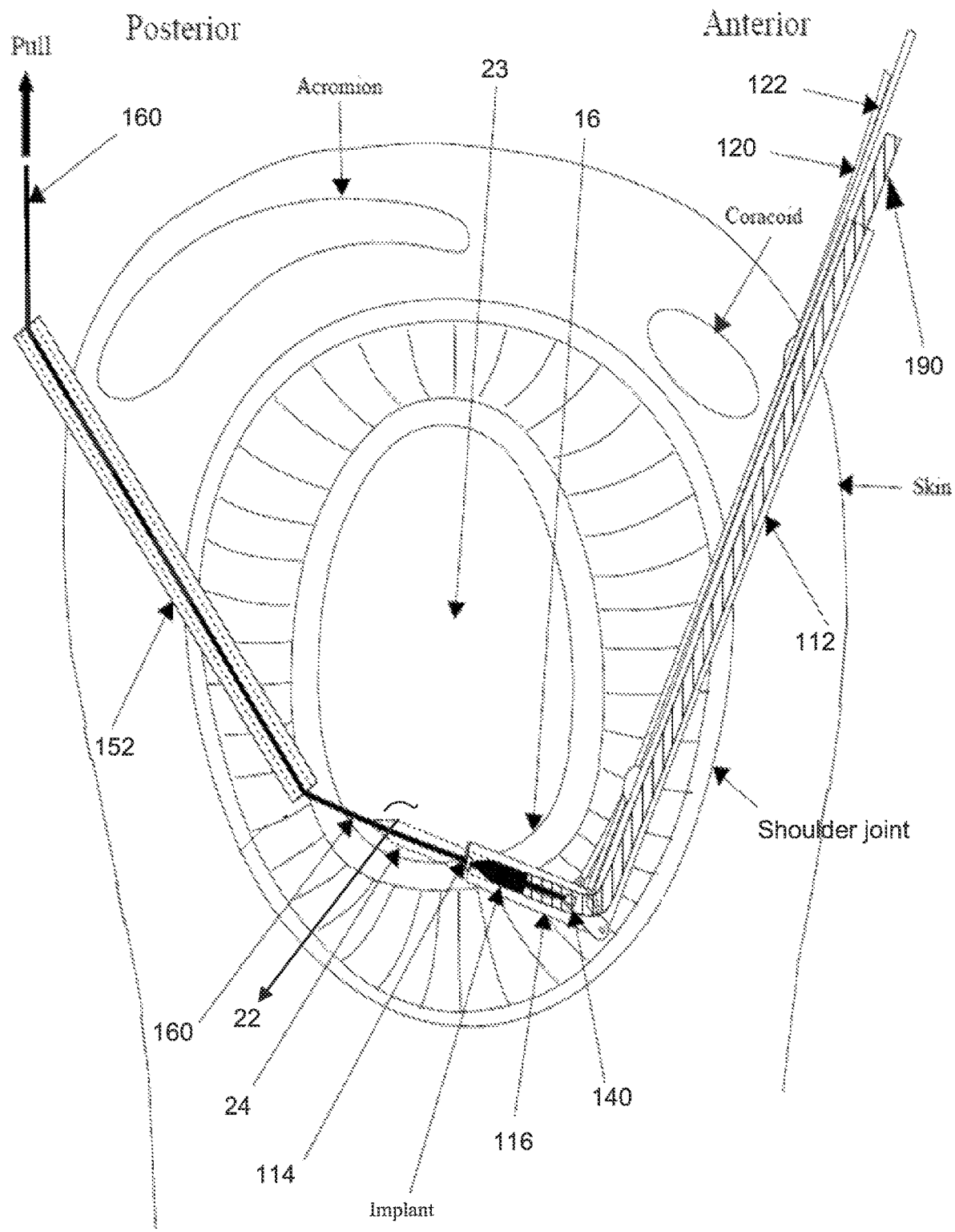

Referring to FIG. 7j, the distal cannula 116 is rotated, for example by the distal cannula control rod 122, to nest within and coaxially align with the slotted cannula 114—to access the pilot hole 24. Once the distal cannula 116 is nested within the slotted cannula 114, the angulation of the distal cannula 116 is locked, for example by the distal cannula control rod 122. The implant shaft 190 may match the angulation of the slotted cannula 114 while nesting within the distal cannula 116.

Figure 7K:
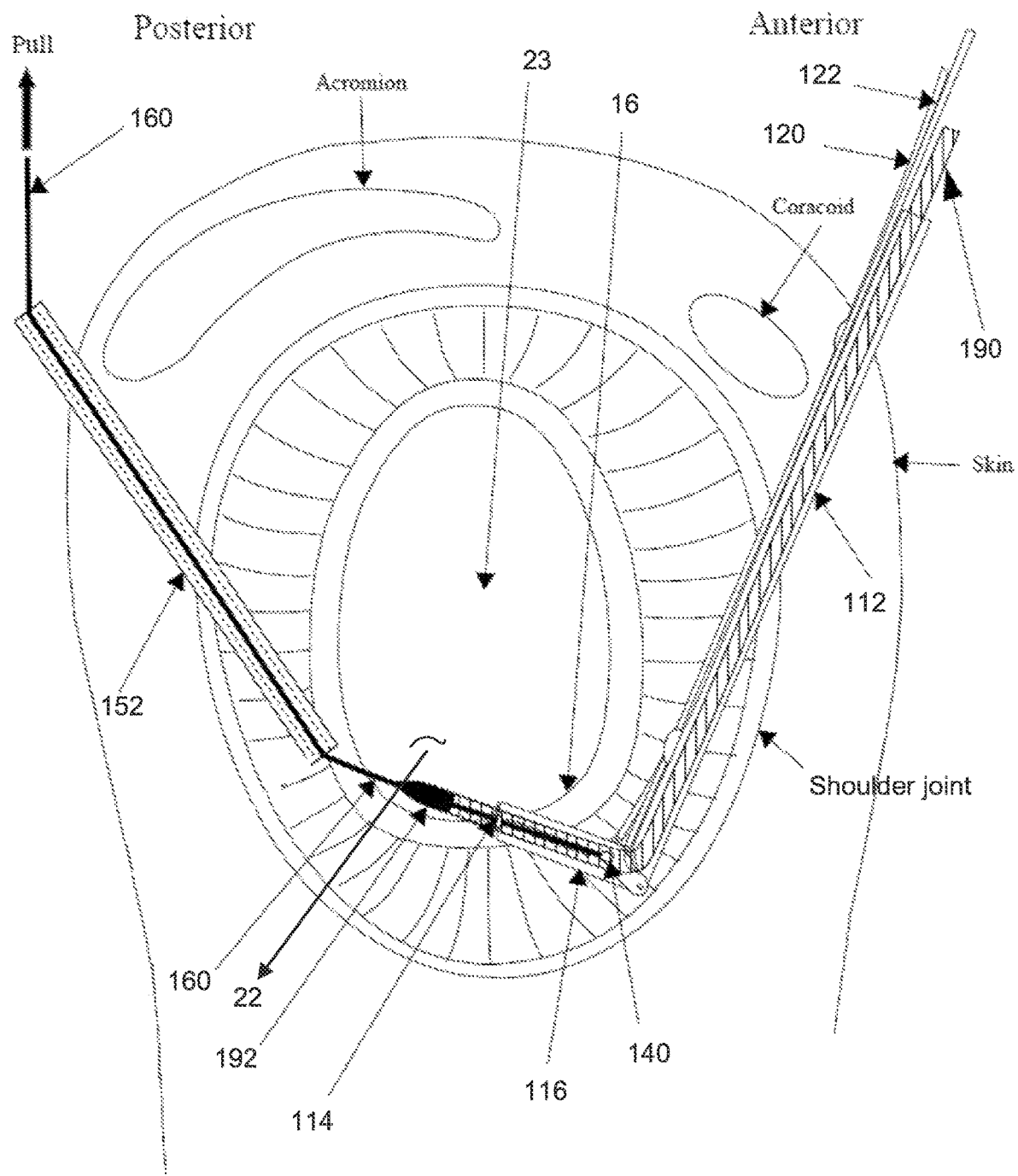
Figure 7I:
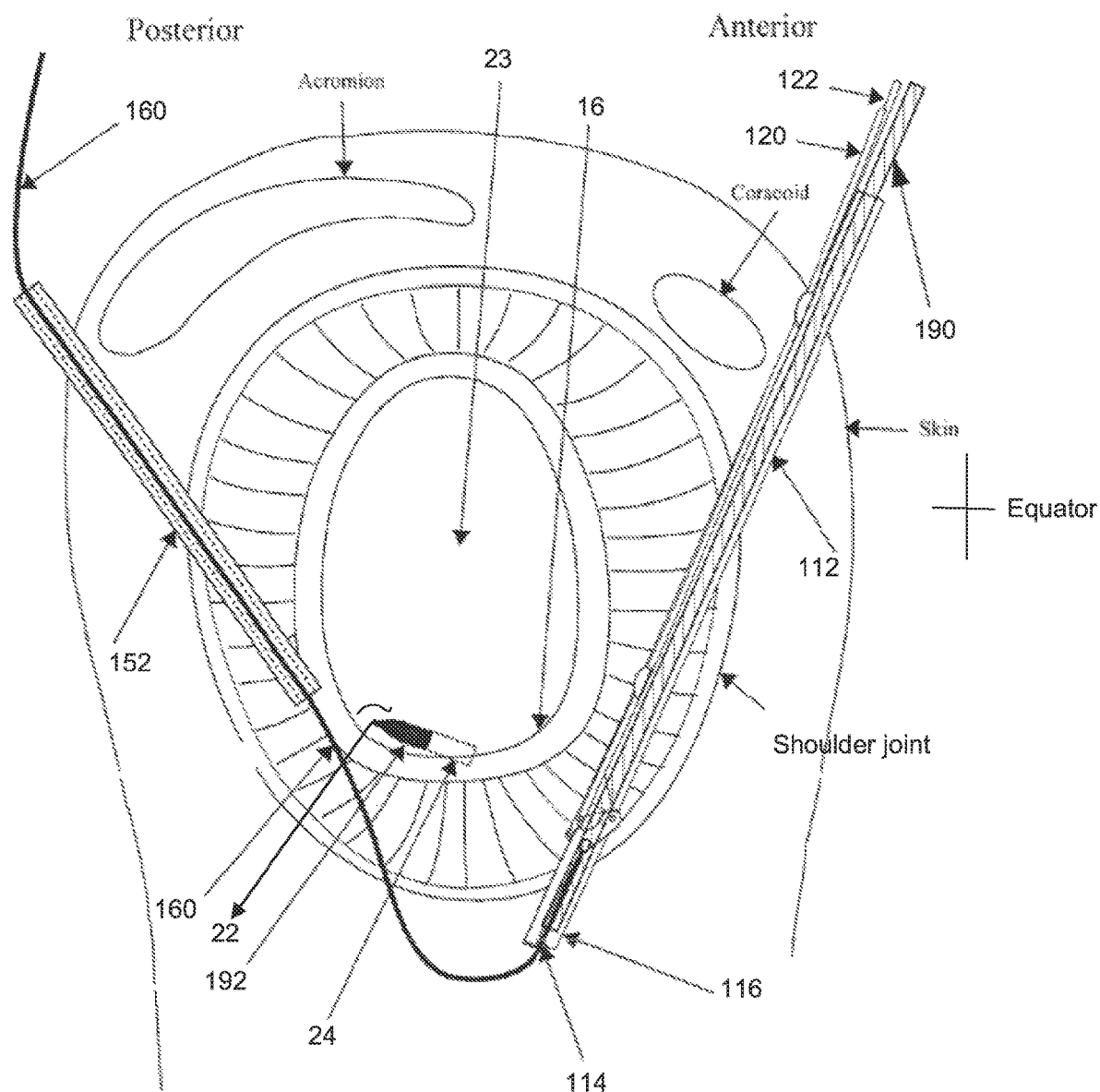

Referring to FIG. 7k, the implant shaft 190 and implant 192 are advanced and extended beyond the slotted cannula 114 and pilot hole 24, by the support from telescoping the implant shaft 190. The implant 192 is inserted into the labrum tear 22. In some embodiments, the implant 192 may be driven or screwed into the labrum tear 22.

Referring to FIG. 7l, the implant shaft 190 is retracted into the distal cannula 116 leaving the implant 192 to repair the labrum tear 22. The tension on the kedging line 160 is released. The slotted cannula 114 and distal cannula 116 are rotated or angulated, for example by slotted cannula control rod 120 and distal cannula control rod 122, respectively, until parallel with the proximal cannula 112.

Figure 8:
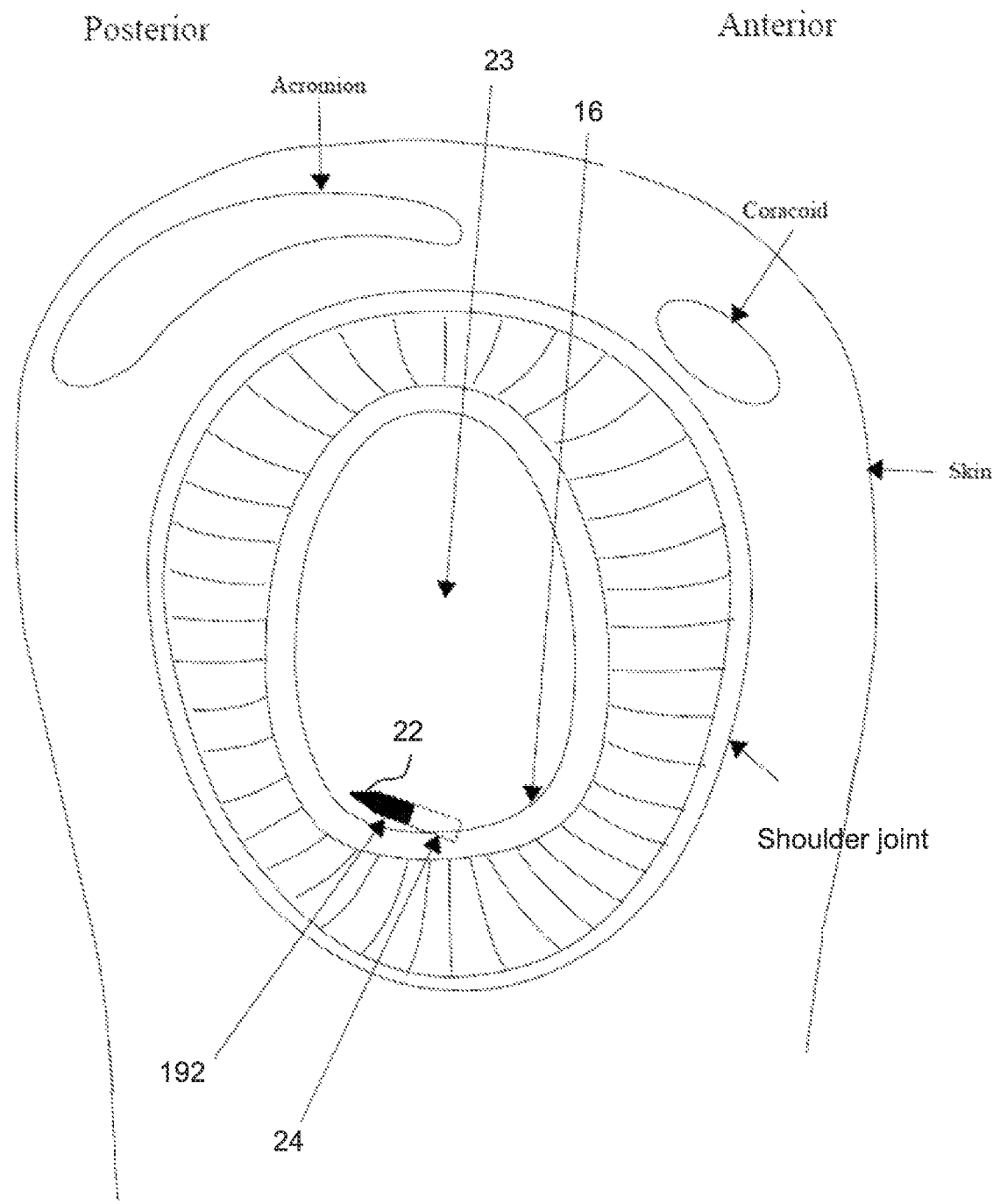
FIG. 8 shows a portion of the shoulder anatomy in which the implant is placed at a site of a labrum tear, according to some embodiments.

Referring to FIG. 8, the guide cannula 150 and kedging line cannula 152 are removed. The implant 110 is left to repair the labrum tear 22.

Figure 9:
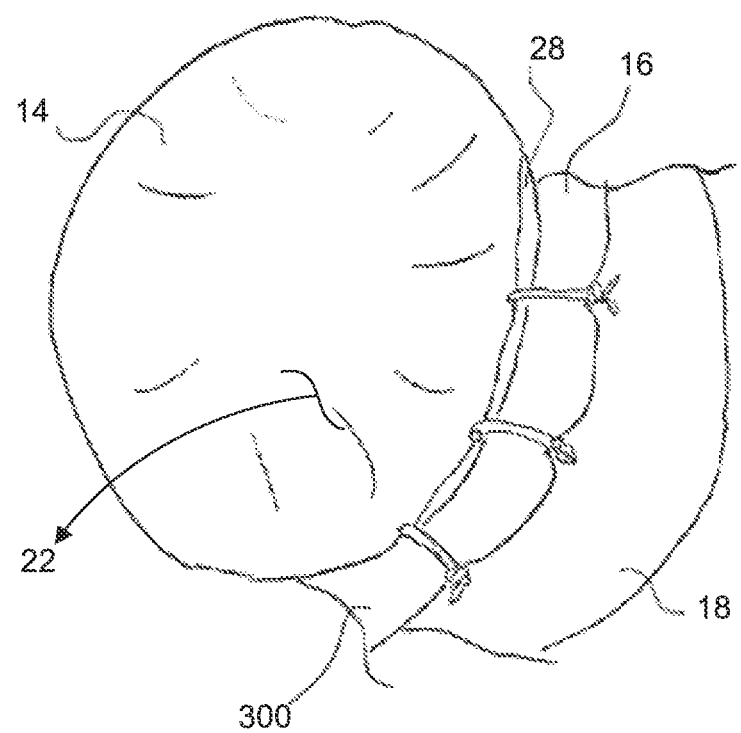
FIG. 9 shows a portion of the shoulder anatomy in which sutures are employed to reattach the labrum, according to some embodiments.

Referring to FIG. 9, in some cases, sutures or anchors 300 may be employed to reattach the torn labrum 16 to the glenoid bone 14 near the glenoid rim 28. In some embodiments, the implant 192 may be attached to one or more sutures or anchors 300 to hold the sutures in place (e.g., in labrum tear 22) and to reattach the torn labrum 16 to the glenoid bone 14. In some embodiments, multiple pilot holes such as pilot hole 24 may be drilled as described in FIGS. 7a-1 for employing multiple sutures or anchors.

This description and the accompanying drawings that illustrate inventive aspects, embodiments, implementations, or applications should not be taken as limiting. Various mechanical, compositional, structural, electrical, and operational changes may be made without departing from the spirit and scope of this description and the claims. In some instances, well-known circuits, structures, or techniques have not been shown or described in detail in order not to obscure the embodiments of this disclosure Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Although illustrative embodiments have been shown and described, a wide range of modifications, changes, and substitutions is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

The invention claimed is:

1. A surgical system, comprising:
a first guide cannula capable of being introduced into an anatomical structure of a human body at a first entry point for repair of a tear in soft tissue;
a second guide cannula capable being introduced into the anatomical structure at a second entry point, wherein a pulling line can be passed within the anatomical structure from the first guide cannula to the second guide cannula; and
a guide device comprising a proximal cannula hingedly connected to a distal cannula and a slotted cannula, the guide device capable of being attached to the pulling line and inserted into the first guide cannula, the guide device capable of delivering a drilling device into the anatomical structure, wherein the direction of the drilling device within the anatomical structure can be adjusted by rotating the distal and slotted cannulas with respect to the proximal cannula;
wherein the pulling line is capable of being pulled to move an end of at least one of the distal cannula and the slotted cannula of the guide device from a first location to a second location within the anatomical structure to position the drilling device on a desired drilling path to access the tear in soft tissue.

2. The system of claim 1, wherein the distal cannula and the slot cannula are capable of rotating independently with respect to the proximal cannula to allow an angular separation between the distal cannula, the slotted cannula, and the proximal cannula.

3. The system of claim 2, wherein the drilling device comprises a rigid cutting head and a flexible shaft connected to the rigid cutting head, and wherein the drilling device is extendable between the distal cannula and the proximal cannula during an angular separation between the distal cannula and the proximal cannula.

4. The system of claim 1, further comprising a slotted cannula control rod coupled to the slotted cannula for controlling an angular separation between the slotted cannula and at least one of the distal cannula and the proximal cannula.

5. The system of claim 4, further comprising a locking component configured to fix the angular separation between the slotted cannula and the at least one of the distal cannula and the proximal cannula.

6. The system of claim 1, further comprising a distal cannula control rod coupled to the distal cannula for controlling an angular separation between the distal cannula and at least one of slotted cannula and the proximal cannula.

7. The system of claim 6, further comprising a locking component configured to fix the angular separation between the distal cannula and the at least one of the slotted cannula and the proximal cannula.

8. The system of claim 1, wherein the slotted cannula comprises a frictional tip capable of engaging a bone in the anatomical structure.

9. The system of claim 1, wherein the guide device is further capable of delivering a surgical implant for repair of the tear in soft tissue.

10. The system of claim 1, wherein the slotted cannula is shaped so that the distal cannula can be nested within the slotted cannula when the slotted cannula and the distal cannula are at the same angulation with respect to the proximal cannula.

\* \* \* \* \*